United States Patent
Harks et al.

(10) Patent No.: US 9,763,642 B2
(45) Date of Patent: Sep. 19, 2017

(54) PROPERTY DETERMINATION APPARATUS FOR DETERMINING A PROPERTY OF AN OBJECT

(75) Inventors: Erik Godefridus Antonius Harks, Rijen (NL); Rami Nachabe, Eindhoven (NL); Bernardus Hendrikus Wilhelmus Hendriks, Eindhoven (NL); Szabolcs Deladi, Veldhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 697 days.

(21) Appl. No.: 13/878,585

(22) PCT Filed: Oct. 11, 2011

(86) PCT No.: PCT/IB2011/054474
§ 371 (c)(1),
(2), (4) Date: Apr. 10, 2013

(87) PCT Pub. No.: WO2012/049621
PCT Pub. Date: Apr. 19, 2012

(65) Prior Publication Data
US 2013/0204134 A1    Aug. 8, 2013

(30) Foreign Application Priority Data
Oct. 14, 2010   (EP) .................................... 10187550

(51) Int. Cl.
*A61B 8/00* (2006.01)
*A61B 5/00* (2006.01)
(Continued)

(52) U.S. Cl.
CPC .......... *A61B 8/4416* (2013.01); *A61B 5/0035* (2013.01); *A61B 5/0084* (2013.01);
(Continued)

(58) Field of Classification Search
USPC ......................................... 600/439, 476, 104
See application file for complete search history.

(56) References Cited

U.S. PATENT DOCUMENTS

| 6,436,095 B1 | 8/2002 | Ben-Haim et al. |
| 6,749,344 B2 | 6/2004 | Hamm et al. |

(Continued)

FOREIGN PATENT DOCUMENTS

| DE | 10120787 A1 | 4/2001 |
| JP | 200961342 A | 9/2010 |

(Continued)

OTHER PUBLICATIONS

S.G. Demos et al., "Real Time Assessment of RF Cardiac Tissue Ablation with Optical Spectroscopy", Optics Express, Sep. 15, 2008, vol. 16, No. 19.

(Continued)

*Primary Examiner* — Christopher Cook
*Assistant Examiner* — Carolyn Pehlke

(57) ABSTRACT

The invention relates to a property determination apparatus (1) for determining a property of an object (3). Optical sensing data being indicative of an optical property of the object and ultrasound sensing data being indicative of an ultrasound property of the object are generated, and a property determination unit (75) determines a property of the object based on at least one of the optical sensing data and the ultrasound sensing data. Since light and ultrasound have generally different penetration depths and scattering properties with respect to the object, a property of the object can be determined with good quality, even if the quality of one of the optical sensing data and the ultrasound sensing data is reduced by, for example, a relatively small penetration depth, or if one of the optical sensing data and the (Continued)

ultrasound sensing data is less suitable for determining a desired property of the object.

10 Claims, 23 Drawing Sheets

(51) Int. Cl.
    *A61B 8/12*         (2006.01)
    *A61B 18/14*       (2006.01)
    *A61B 5/026*       (2006.01)
    *A61B 8/08*         (2006.01)
    *A61B 17/00*       (2006.01)
    *A61B 18/00*       (2006.01)

(52) U.S. Cl.
    CPC .......... *A61B 5/4836* (2013.01); *A61B 5/6852* (2013.01); *A61B 8/12* (2013.01); *A61B 8/445* (2013.01); *A61B 8/4477* (2013.01); *A61B 8/463* (2013.01); *A61B 18/1492* (2013.01); *A61B 5/0261* (2013.01); *A61B 8/486* (2013.01); *A61B 8/5223* (2013.01); *A61B 2017/00061* (2013.01); *A61B 2017/00106* (2013.01); *A61B 2017/00292* (2013.01); *A61B 2018/00357* (2013.01); *A61B 2018/00577* (2013.01); *A61B 2018/00636* (2013.01); *A61B 2218/002* (2013.01)

(56) References Cited

U.S. PATENT DOCUMENTS

| | | | |
|---|---|---|---|
| 7,306,593 B2* | 12/2007 | Keidar | A61B 5/06 606/34 |
| 8,753,281 B2 | 6/2014 | Schmitt et al. | |
| 2006/0229515 A1 | 10/2006 | Shararch et al. | |
| 2008/0039742 A1 | 2/2008 | Hashimshony et al. | |
| 2008/0154257 A1 | 6/2008 | Shararch et al. | |
| 2008/0177183 A1 | 7/2008 | Courtney et al. | |
| 2008/0221448 A1 | 9/2008 | Khuri-Yakub et al. | |
| 2009/0005771 A1 | 1/2009 | Leiber et al. | |
| 2009/0030412 A1* | 1/2009 | Willis | A61B 1/00089 606/41 |
| 2009/0076375 A1 | 3/2009 | Maschke | |
| 2009/0093807 A1 | 4/2009 | Hyde et al. | |
| 2010/0222647 A1 | 9/2010 | Hashimshony et al. | |
| 2010/0249601 A1* | 9/2010 | Courtney | A61B 5/6852 600/463 |
| 2010/0286527 A1* | 11/2010 | Cannon | A61B 7/04 600/459 |
| 2012/0184953 A1* | 7/2012 | Spence | A61B 18/1492 606/41 |

FOREIGN PATENT DOCUMENTS

| | | | | |
|---|---|---|---|---|
| WO | WO 2008090484 A2 * | 7/2008 | .......... | G06T 7/0012 |
| WO | WO2010011820 | 1/2010 | | |
| WO | WO2010082146 | 7/2010 | | |
| WO | WO 2010103423 A2 * | 9/2010 | | |

OTHER PUBLICATIONS

I. Fredriksson et al., "Optical Microcirculatory Skin Model: Assessed by Monte Carlo Simulations Paired with In Vivo Laser Flowmetry", Journal of Biomedical Optics 13(1), Jan./Feb. 2008, pp. 014015-1-014015-12.

D.M. Haaland et al., Partial Least-Squares methods for Spectral Analyses. 1. Relation to Other Quantitative Calibration methods and the Extraction of Qualitative Information, Analytical Chemistry, vol. 60, No. 11, Jun. 1, 1988, pp. 1193-1202.

R.M. Haralick et al., "Textural Features for Image Classification", IEEE Transactions on Systems, Man, and Cybernetics, Nov. 1973, pp. 610-621.

R. Nachabe et al., "Estimation of Lipid and Water Concentrations in Scattering Media with Diffuse Optical Spectroscopy from 900 to 1600 nm", Journal of biomedical Optics 15(3), May 1/Jun. 2010, pp. 1-1-1-11.

\* cited by examiner

PROPERTY DETERMINATION APPARATUS FOR DETERMINING A PROPERTY OF AN OBJECT

FIELD OF THE INVENTION

The invention relates to a property determination apparatus, a property determination method and a property determination computer program for determining a property of an object.

BACKGROUND OF THE INVENTION

US 2006/0229515 A1 discloses an optical method and apparatus utilized to evaluate the presence of tissue modification, in particular, to evaluate tissue ablation using light scattering spectroscopy realized via optical fibers. The evaluation of tissue ablation by using light scattering spectroscopy is relatively inaccurate, because of the small penetration depth of the light into the tissue and because of significant variations in tissue structure and tissue perfusion, which adversely affect the interpretation of light scattering spectra.

SUMMARY OF THE INVENTION

It is an object of the present invention to present a property determination apparatus, a property determination method and a property determination computer program, for determining a property of an object, wherein the determination of a property of an object can be improved.

In a first aspect of the present invention a property determination apparatus for determining a property of an object is presented, wherein the property determination apparatus comprises:
an optical sensor for generating optical sensing data being indicative of an optical property of the object,
an ultrasound sensor for generating ultrasound sensing data being indicative of an ultrasound property of the object,
a property determination unit for determining a property of the object based on at least one of the optical sensing data and the ultrasound sensing data.

Since light and ultrasound have generally different penetration depths and scattering properties with respect to the object, by providing a property determination apparatus, which comprises an optical sensor for generating optical sensing data, an ultrasound sensor for generating ultrasound sensing data and a property determination unit for determining a property of the object based on at least one of the optical sensing data and the ultrasound sensing data, a property of the object can be determined with good quality, even if the quality of one of the optical sensing data and the ultrasound sensing data is reduced by, for example, a relatively small penetration depth, or if one of the optical sensing data and the ultrasound sensing data is less suitable for determining a desired property of the object. This can improve the quality of determining the property of the object.

It is preferred that the property determination apparatus comprises a catheter, wherein the optical sensor and the ultrasound sensor are integrated in the catheter, i.e. at least a part of the optical sensor and the ultrasound sensor is integrated in the catheter. For example, the optical sensor can comprise optical fibers which are integrated together with one or several ultrasound transducers, i.e. one or several ultrasound sensors, in the catheter. The catheter allows the optical sensor and the ultrasound sensor to be introduced into, for example, a person or an animal, in order to determine a property of a wall of a heart or of another organ.

It is further preferred that the property determination apparatus comprises an energy application element for applying energy to the object. Also the energy application element is preferentially integrated in the catheter which includes the optical sensor and the ultrasound sensor. Thus, the catheter can be introduced into a person or into an animal, wherein energy can be applied to, for example, the wall of the heart or of another organ and a property of the wall can be determined at the location at which energy is applied. The property can be determined before the energy is applied, while the energy is applied and/or after the energy has been applied. The energy is preferentially ablation energy for ablating tissue, in particular, for ablating cardiac tissue of a wall of a heart. The energy application element is, for example, a radiofrequency (RF) electrode for applying RF energy. However, the energy application element can also be adapted to apply another kind of energy to the object like coldness for performing cryo ablation, light for performing an optical ablation, et cetera.

The optical sensor comprises preferentially a light emitting means for illuminating the object by light and a light receiving means for receiving light from the object, wherein the optical sensor is adapted to generate optical sensing data depending on the received light. Preferentially, the light emitting means comprises one or several optical fibers for illuminating the object at different positions and one or several optical fibers for receiving light from the object. The one or several optical fibers for illuminating the object are connected to a light source like a laser, wherein the optical fibers guide the light from the light source to the object. The one or several optical fibers for receiving light from the object are preferentially connected to a spectrometer for generating one or several optical spectra of the object, wherein the property determination unit is preferentially adapted to determine a property of the object depending on the one or several optical spectra.

It is further preferred that the property determination unit is adapted to determine a property of a surface of the object from the optical sensing data. The optical sensing data are preferentially one or several optical spectra, wherein the optical spectra are indicative of the absorption and/or scattering properties of the object and can therefore be used to determine scattering and/or absorption properties of the object or further properties of the object which influence the scattering and/or absorption properties of the object. For example, based on the optical spectra it can be determined whether cardiac tissue is ablated or non-ablated. The optical spectra can also be used to determine the kind of object or the composition of the object sensed by the optical sensor. The property determination apparatus can therefore be adapted to distinguish ablated tissue from non-ablated tissue or to determine the kind of object or the composition of the object sensed by the optical sensor based on the optical sensing data. In an embodiment, the property determination unit comprises a memory, in which optical spectra are stored, which are assigned to, for example, ablated tissue or non-ablated tissue. The property determination unit is preferentially adapted to compare the stored optical spectra with actually measured optical spectra, in order to determine whether the optically sensed object has been ablated or not. Correspondingly, the property determination unit can comprise a memory, in which optical spectra are stored, which are assigned to different kinds of objects or to different possible elements of an object, wherein the property determination unit can be adapted to determine the respective kind of object or the composition of the object by comparing the stored optical spectra with actually measured optical spectra.

It is further preferred that energy has been applied to the object along a line by an energy application element, wherein the property determination unit is adapted to determine whether energy has been applied continuously along the line as the property of the object depending on the optical sensing data. It is further preferred that the optical sensor is adapted to generate optical spectra at several positions along the line and to determine whether energy has been applied continuously along the line depending on the generated optical spectra. Preferentially, one or several optical sensors of the property determination apparatus are moved along the line, in order to measure optical spectra along this line. The property determination apparatus is preferentially adapted to determine whether, for example, tissue is continuously ablated along the line based on the measured optical spectra. Thus, the optical sensor and the property determination unit can be used for evaluating an ablation line, in particular, for determining whether tissue has been ablated continuously along an ablation line.

It is further preferred that the object is perfused by a fluid, wherein the property determination unit is adapted to determine a degree of perfusion of the object from the optical sensing data. The property determination apparatus can be adapted to determine the degree of perfusion by using Laser Doppler Flowmetry (LDF). If the object is a wall of a heart or of another organ, the determined degree of perfusion can be used to detect anomalies in the blood perfusion of tissue, in particular, of cardiac tissue, which can be addressed by segmenting scar tissue, for example, after a myocardic infarct, by using ablation. If the property determination apparatus is adapted to perform LDF for determining the degree of perfusion, the optical sensor comprises preferentially at least three optical fibers, one illumination fiber for illuminating the object and two receiving fibers for receiving light from the object, wherein the illumination fiber is placed at different distances from the two receiving fibers.

It is further preferred that the property determination unit is adapted to determine a depth influence value being indicative of a depth to which the object has been influenced by the applied energy. The depth influence value is, for example, a lesion depth or a degree of transmurality with respect to a wall of a heart or of another organ. The energy application element can be adapted to be controlled depending on the depth influence value, in particular, depending on the development of a lesion, which is defined by the lesion depth and caused by the respective energy application element. Thus, local lesion progression can be determined and the energy application element can be controlled based on the determined local lesion progression.

In an embodiment, the ultrasound sensing data are an ultrasound signal representing ultrasound reflection properties of the object at different depths, wherein the property determination unit is adapted to determine a discontinuity of the ultrasound signal and to determine the lesion depth as the depth of the ultrasound signal at which the discontinuity occurs. The ultrasound signal preferably also represents the ultrasound reflection properties at different times, thereby allowing determining the lesion depth at different times, in particular, in realtime. This allows controlling the energy application element in realtime depending on the local lesion depth, in particular, such that an overtreatment like an overheating and an undertreatment are prevented.

The property determination unit can be adapted to correct the ultrasound signal for a thermal expansion of the object caused by the ablation procedure and to determine the lesion depth and an ablation time as the depth and the time of temporally subsequent signal values of the corrected ultrasound signal, which correspond to the same depth and which are not similar with respect to a predefined similarity measure. In particular, the property determination unit can also be adapted to:
correct the ultrasound signal for a thermal expansion of the object caused by the ablation procedure,
determine stretches comprised of temporally subsequent signal values of the corrected ultrasound signal, which correspond to the same depth and which are similar with respect to a similarity measure,
determine the lesion depth and an ablation time as the depth and the time at which the length of the stretches is below a predefined threshold. This predefined threshold can be determined by a calibration measurement, wherein ultrasound signals are generated by sending ultrasound pulses into the object having a known lesion depth. In an embodiment, stretches having a length larger than 0.25 s, further preferred larger than 0.5 s and even further preferred larger than 1 s, are regarded as indicating that an ablation has not yet occurred at the respective depth.

In an embodiment, the property determination unit is adapted to:
correct the ultrasound signal for a thermal expansion of the object caused by the ablation procedure,
determine, for different depth regions and at the different times, a cross correlation of temporally subsequent signal values of the same depth region,
determine a lesion depth and an ablation time depending on the cross correlation of the temporally subsequent signals determined for the different depth regions and at the different times. In particular, the property determination unit is adapted to determine, for different depth regions and at the different times, a shift value depending on the determined cross correlation and to determine a lesion depth and an ablation time depending on the determined shift values, wherein a shift value is indicative of a shift between temporally subsequent signals within a depth region.

The ultrasound signal representing ultrasound reflection properties of the object at different depths and at different times is preferentially an M-mode image.

The cross correlation is preferably performed in the Fourier domain, i.e. preferentially before determining the cross correlation the ultrasound signal is Fourier transformed, and after the cross correlation has been determined and before the shift values are determined an inverse Fourier transformation is preferentially performed. This performing of the cross correlation in the Fourier domain results in faster processing.

Preferentially, the depth dimension is subdivided into different depth regions, wherein for each depth region each line of signal values defined by the same time is cross correlated with its temporally preceding line of signal values which belong to the same preceding time. Thus, for the respective depth region a number of cross correlation lines is determined. The cross correlation lines of the respective depth region are preferentially averaged. This averaging is preferentially performed by applying an average filter to the cross correlation lines of the respective depth region.

The shift value at a depth region and at a time is preferentially determined by determining a peak of the cross correlation line of the respective depth region at the respective time. The depth position of the respective peak within the respective depth region is indicative of the shift between the two lines of signal values within the depth region, which have been cross correlated for determining the cross correlation line. The shift value is therefore preferentially determined from the depth position of the peak within the respective depth region. The accuracy of determining the depth position of the peak within the respective depth region is preferentially improved by fitting a parabola to the peak, wherein the maximum of the parabola is used as the depth position of the peak within the depth region. Preferentially, the peak is cut out of the respective cross correlation line before performing the fitting procedure, in order to fit the parabola to the peak only and not to the respective complete cross correlation line within the respective depth region.

For determining the lesion depth and the ablation time a thresholding is preferentially performed on the determined shift values. In an embodiment, if a shift value is larger than a predefined shift threshold, the corresponding depth region and time are preferentially regarded as lesion depth, at which the ablation process occurs, and as ablation time. A zone where tissue is coagulating corresponds to a region of poor cross correlation, i.e. corresponds to a region of a relatively large shift value. A healthy tissue zone and a zone including tissue that is already completely coagulated correspond to regions of good cross correlation, i.e. correspond to regions of a relatively small shift value. The zone at which tissue is actually coagulating can therefore be separated from a healthy tissue zone and a zone comprising tissue that is already completely coagulated by using the predefined shift threshold. This shift threshold can be predefined by, for example, calibration.

The ultrasound sensing data, i.e. the ultrasound signal, is preferentially generated by sending an ultrasound pulse out the object, receiving echo series from the object, and generating the ultrasound signal depending on the received echo series. In an embodiment, the property determination unit determines at least one scatter value being indicative of a scatter of the ultrasound pulse by a fluid perfusing the object, wherein the property determination unit is adapted to determine the at least one scatter value depending on the ultrasound signal and to determine a property of the object depending on the at least one scatter value.

The property determination unit can be adapted to determine several scatter values to determine the property based on the several scatter values.

The object is preferentially an organ of a person or of an animal, wherein the organ is perfused by a bodily fluid like blood. In particular, the object is preferentially the heart, wherein the tissue of the heart is perfused by blood. It is preferred that the property determination unit is adapted to determine a degree of perfusion, in particular, capillary perfusion, of the object by the fluid as the property based on the at least one scatter value. In particular, the property determination unit is adapted to determine which part of the object is perfused and which part of the object is not perfused. Since the at least one scatter value is indicative of a scatter of the ultrasound pulse by the fluid, the degree of perfusion of the object, in particular, whether the object or a part of the object is perfused or not perfused, can be determined based on the at least one scatter value, i.e. if the object is not perfused by fluid, the property determination unit can determine a scatter value being indicative of the absence of the fluid, and, for example, that the object is not perfused, and if the object is perfused by fluid, the property determination unit can determine a scatter value being indicative of the presence of the fluid, and, for example, that the object is perfused.

Since the ultrasound signal is provided for different depths within the object, the property determination unit can determine whether the object is perfused or whether the object is not perfused for different depths of the object, in particular, for different depths within the inner wall of the heart, as the depth influence value. In particular, the property determination unit can determine at which depth the inner wall of the heart is ablated and at which depth the inner wall of the heart is non-ablated depending on the at least one scatter value determined for the respective depth. Depending on this information the property determination unit can determine the lesion depth, i.e. since, after it has been determined which part of the tissue is ablated tissue and which part of the tissue is non-ablated tissue, the spatial distribution of ablated and non-ablated regions within the tissue is known, the lesion depth can easily be determined from the determined ablated and non-ablated parts of the tissue.

By ablation the perfusion of the object can be modified, wherein the modification of the perfusion can modify the scattering of the ultrasound pulse by the fluid and, thus, the at least one scatter value. The modification of the at least one scatter value can therefore be used for determining the degree of ablation. For instance, by calibration measurements it can be determined which scatter values, or which changes of scatter values after an ablation procedure has been started, correspond to which degrees of ablation, wherein the scatter values are determined, while the degree of ablation is known. These determined scatter values can be regarded as calibration values, wherein the calibration values can then be used for determining the degree of ablation depending on actually determined scatter values.

It is further preferred that the provided ultrasound signal represents the scattering by the fluid at at least one of a) different depths within the object and b) different times, wherein the ultrasound signal is sampled by sample windows corresponding to the at least one of a) different depths and b) different times, wherein the scatter value determination unit is adapted to determine scatter values for the sample windows, wherein for a respective sample window at least one scatter value is determined based on the part of the ultrasound signal which corresponds to the respective sample window, wherein the property determination unit is adapted to determine a property for the respective sample window based on the at least one scatter value determined for the respective sample window. If, for example, the ultrasound signal is an M-mode image, the M-mode image can be sampled by several sample windows corresponding to certain depth ranges and to certain time ranges. For each of the sample windows at least one scatter value can be determined, wherein for each of the sample windows a property, in particular, whether the tissue within the respective sample window is ablated or non-ablated, can be determined based on the at least one scatter value determined for the respective sample window. This allows monitoring the property over time and in different depths. In particular, the property can be monitored in realtime. For example, the lesion depth may be monitored in realtime.

The sample windows are preferentially overlapping, because then the resolution of determining the property of the object can be increased, without reducing the sample window size. However, the sample windows can also be non-overlapping.

It is further preferred that each of the sample windows corresponds to several ultrasound intensities of the ultrasound signal, wherein the property determination unit is adapted to determine at least one scatter value for a sample window depending on a histogram of the ultrasound intensities within the respective sample window. Thus, preferentially for each of the sample windows at least one scatter value is determined depending on a histogram of the ultrasound intensities of the respective sample window. In particular, the property determination unit is adapted to determine the at least one scatter value based on at least one of a first-order histogram and a second-order histogram. Also higher-order statistics can be used for determining the at least one scatter value, for example, a Gabor filtering approach can be used for determining the at least one scatter value.

It is further preferred that the property determination unit is adapted to determine at least one of the following values as the at least one scatter value: a first-order mean of the first-order histogram, a first-order variance of the first-order histogram, a first-order entropy of the first-order histogram, a second-order entropy of the second-order histogram, a second-order energy of the second-order histogram, a second-order homogeneity of the second-order histogram, a second-order contrast of the second-order histogram, a second-order cluster tendency of the second-order histogram, a second-order shape of the second-order histogram, a second-order correlation of the second-order histogram and a second-order correlation derivative of the second-order histogram.

In an embodiment, each of the sample windows corresponds to several ultrasound intensities of the ultrasound signal, wherein the property determination unit is adapted to determine at least one scatter value for a sample window depending on a summation of the ultrasound intensities within the respective sample window. Thus, in addition to or in an alternative to using histogram-based scatter values, also scatter values can be used, which depend on a summation of the ultrasound intensities within the respective sample window. For example, a scatter value can be the sum over all ultrasound intensities within a respective sample window or the sum over products of ultrasound intensities, wherein at least one of the ultrasound intensities of each pair is located within the respective sample window and wherein each product comprises ultrasound intensities which correspond to acquisition times, which are separated by a heart cycle period of the object, if the object is cardiac tissue. If histogram-based scatter values and these summation-based scatter values, which are preferentially not based on a histogram, are used together for determining the property of the object, the accuracy of determining the property of the object can be further improved.

It is further preferred that the property determination unit is adapted to apply a cluster analysis to the sample windows, wherein the sample windows are clustered depending on the at least one scatter value determined for the respective sample window, and to assign properties to the clusters of sample windows. The property determination unit can be adapted to perform a clustering algorithm like a K-means clustering for grouping the scatter values. If for each sample window only a single scatter value has been determined, the clustering algorithm is applied to the single scatter values, and, if for each sample window several scatter values have been determined, the scatter values which have been determined for a single sample window form a multi-dimensional feature vector and the clustering algorithm is applied to the multi-dimensional feature vectors determined for the several sample windows. The clustering algorithm can result in a first cluster of scatter values or multi-dimensional feature vectors, respectively, and, thus, in a corresponding first cluster of sample windows and in a second cluster of scatter values or multi-dimensional feature vectors, respectively and, thus, in a corresponding second cluster of sample windows. The first cluster of sample windows can represent ablated tissue and the second cluster of sample windows can represent non-ablated tissue. Whether a cluster represents ablated or non-ablated tissue can be determined depending on a comparison with a threshold, which can be determined by calibration measurements. Thus, the assignment of properties of the object to the cluster of sample windows can be performed by thresholding. It is also possible that the cluster analysis is firstly applied before ablation is started, leading to a first group of clusters representing non-ablated tissue. Then, the clustering analysis is continuously applied, while the ablation procedure is performed. If the clustering analysis leads to new clusters, which do not belong to the first group of clusters, the property "ablated tissue" can be assigned to these new clusters.

The property determination unit can be adapted to determine the property based on a comparison of the at least one scatter value with at least one threshold value. For example, the ultrasound signal can be sampled by using the above mentioned sample windows and for each sample window at least one scatter value can be determined. It can be defined that, if a scatter value of a sample window is above a threshold value, the tissue, which corresponds to the sample window, is non-ablated, and that, if the scatter value is below the threshold value, the tissue, which corresponds to this sample window, is ablated. If several scatter values have been determined for the same sample window, for each scatter value a threshold value can be provided and for each scatter value it can be determined whether the respective scatter value is above or below the respective threshold value. If, for example, the majority of scatter values of a sample window is above the respective threshold value, it can be defined that the tissue, which corresponds to the sample window, is non-ablated, and if, for example, the majority of scatter values is below the respective threshold value, it can be defined that the tissue, which corresponds to the sample window, is ablated. The one or several thresholds can be determined by, for example, calibration measurements. If for a sample window several scatter values are determined, they can be combined to a multi-dimensional feature vector, i.e. for each sample window a multi-dimensional feature vector can be defined, wherein the multi-dimensional feature vector can be compared with a threshold vector for determining whether the respective sample window corresponds to ablated tissue or to non-ablated tissue.

It is further preferred that the ultrasound sensor can be adapted to provide an ultrasound signal produced by using ultrasound waves with a frequency being larger than 10 MHz. The ultrasound waves have preferentially a frequency within a frequency range of 20 to 40 MHz, in particular, a frequency of 30 MHz. Using these relatively high ultrasound frequencies leads to an increased resolution of the ultrasound signal. Since the resolution of the ultrasound signal is increased, patterns in the ultrasound signal, which are caused by scattering of the ultrasound pulse by the fluid, are better recognizable in the ultrasound signal. The extraction of the at least one scatter value from the ultrasound signal and, thus, the quality of the determined property are therefore improved.

The property determination unit is preferentially further adapted to determine an object wall thickness at the location at which the energy application element applies energy from the ultrasound signal and to determine the degree of transmurality based on the lesion depth and the object wall thickness.

It is further preferred that energy is applied to the object by using an energy application element, wherein the property determination apparatus further comprises a contact determination unit for determining whether the energy application element is in contact with the object based on the ultrasound sensing data. This allows controlling the application of energy depending on whether the energy application element is in contact with the object or not. In particular, the application of energy can be controlled such that energy is applied to the object only, if the energy application element is in contact with the object, thereby improving the quality of applying energy to the object.

It is further preferred that the property determination apparatus comprises at least two ultrasound sensors being adapted to sense the object in different sensing directions, wherein the property determination apparatus further comprises an ultrasound sensor selection unit for selecting an ultrasound sensor from the at least two ultrasound sensors depending on the generated optical sensing data and wherein the property determination unit is adapted to determine the property of the object depending on the ultrasound sensing data of the selected ultrasound sensor. Preferentially, the ultrasound sensor selection unit is adapted to determine the orientations of the sensing directions relative to the object from the optical sensing data and to select an ultrasound sensor based on the determined orientations. The property determination apparatus can comprise several optical sensors, wherein the spatial relationship between the several optical sensors and the sensing directions of the ultrasound sensors is known and wherein the ultrasound sensor selection unit is adapted to determine optical sensor contact information being indicative of which optical sensors are in contact with the object, determine the orientations of the sensing directions of the ultrasound sensors relative to the object depending on the optical sensor contact information and the spatial relationship between the several optical sensors and the sensing directions of the ultrasound sensors. The ultrasound sensor selection unit is preferentially adapted to select the ultrasound sensor of which the sensing direction is most perpendicular to a surface of the object. In particular, the ultrasound sensor selection unit is adapted to select the ultrasound sensor of which the sensing direction is most perpendicular to a surface of the object to which energy has been applied. The ultrasound sensing data are preferentially used for determining a property of the object depending on the depth. By selecting an ultrasound sensor having a sensing direction being most perpendicular to a surface of the object, the depth dependence of the property can more reliably be determined.

It is further preferred that the property determination apparatus comprises a display for displaying at least one of the optical sensing data, the ultrasound sensing data, and the determined property of the object. In an embodiment, energy can be applied to the object at an energy application location on the object, wherein the optical sensor is adapted to generate optical sensing data being indicative of an optical property of the object at the energy application location, wherein the ultrasound sensor is adapted to generate ultrasound sensing data at the energy application location, wherein the property determination unit is adapted to determine a property of the object based on at least one of the optical sensing data and the ultrasound sensing data at the energy application location, wherein the property determination apparatus further comprises:

a storage unit for storing at least one of the optical sensing data, the ultrasound sensing data and the determined property, an image providing unit for providing an image of the object, wherein the display is adapted to display the energy application location on the image, a user interface for allowing a user to select the shown energy application location, wherein the display is adapted to display at least one of the optical sensing data, the ultrasound sensing data and the determined property, if the displayed energy application location has been selected by the user. This allows a user to study the optical sensing data, the ultrasound sensing data and/or the determined property of the object, which correspond to the selected energy application location. Also determined orientations can be stored in the storage unit and displayed, if the corresponding energy application location has been selected.

It is further preferred that the property determination apparatus comprises an energy application plan providing unit for providing an energy application plan comprising energy application locations at which energy is to be applied to the object, an energy application element for applying energy to the object at the energy application locations, a contact determination unit for determining whether the energy application element is in contact with the object based on the ultrasound sensing data, a moving unit for moving the energy application element, the optical sensor and the ultrasound sensor to an energy application location of the energy application plan, a control unit for controlling the property determination apparatus in accordance with following steps:

a) providing an energy application plan comprising energy application locations at which energy is to be applied to the object by the energy application plan providing unit, b) moving the energy application element, the optical sensor and the ultrasound sensor to an energy application location of the energy application plan by the moving unit, c) generating ultrasound sensing data at the energy application location by the ultrasound sensor, d) determining whether the energy application element is in contact with the object at the energy application location based on the ultrasound sensing data, wherein, if the energy application element is not in contact with the object, the position of the energy application element is modified by the moving unit and steps c) and d) are repeated, until the energy application element is in contact with the object, e) generating optical sensing data at the energy application location by the optical sensor, f) determining whether the object has already been influenced by energy at the energy application location by the property determination unit depending on the optical sensing data, wherein, if the object has already been influenced by energy at the energy application location, the method continuous with step b) for moving the energy application element, the optical sensor and the ultrasound sensor to a next energy application location of the energy application plan, g) applying energy to the object at the energy application location, h) generating ultrasound sensing data at the energy application location by the ultrasound sensor, i) determining whether the object has been influenced by energy to a predefined degree at the energy application location by the property determination unit depending on the ultrasound sensing data, wherein steps g) to i) are repeated, until the object has been influenced by energy to the predefined degree at the energy application location, j) repeating steps b) to i) with a next energy application location of the energy application plan, until energy has been applied to all energy application locations of the energy application plan. This ensures that at all energy application locations of the object have been influenced to the predefined degree, in particular, such that it is transmural at the energy application locations, by using the ultrasound sensing data. The optical sensing data are used for determining whether energy has already been applied at an energy application location and the optical sensing data can also be used for determining whether, after the energy has been applied to all planned energy application locations, the regions, which have been influenced by energy to the predefined degree, form a continuous line. It can therefore be ensured that a continuous line has been generated, along which the object has been influenced by energy to a predefined degree, in particular, along which the object, which is preferentially a wall of a heart or of another organ, is continuously transmural.

In a further aspect of the present invention a property determination method for determining a property of an object is presented, wherein the property determination method comprises:

generating optical sensing data being indicative of an optical property of the object by an optical sensor, generating ultrasound sensing data being indicative of an ultrasound property of the object by an ultrasound sensor, determining a property of the object based on at least one of the optical sensing data and the ultrasound sensing data by a property determination unit.

In a further aspect of the present invention a property determination computer program for determining a property of an object is presented, wherein the property determination computer program comprises program code means for causing a property determination apparatus as defined in claim 1 to carry out the steps of the property determination method as defined in claim 14, when the computer program is run on a computer controlling the property determination apparatus.

It shall be understood that the property determination apparatus of claim 1, the property determination method of claim 14, and the property determination computer program of claim 15 have similar and/or identical preferred embodiments, in particular, as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
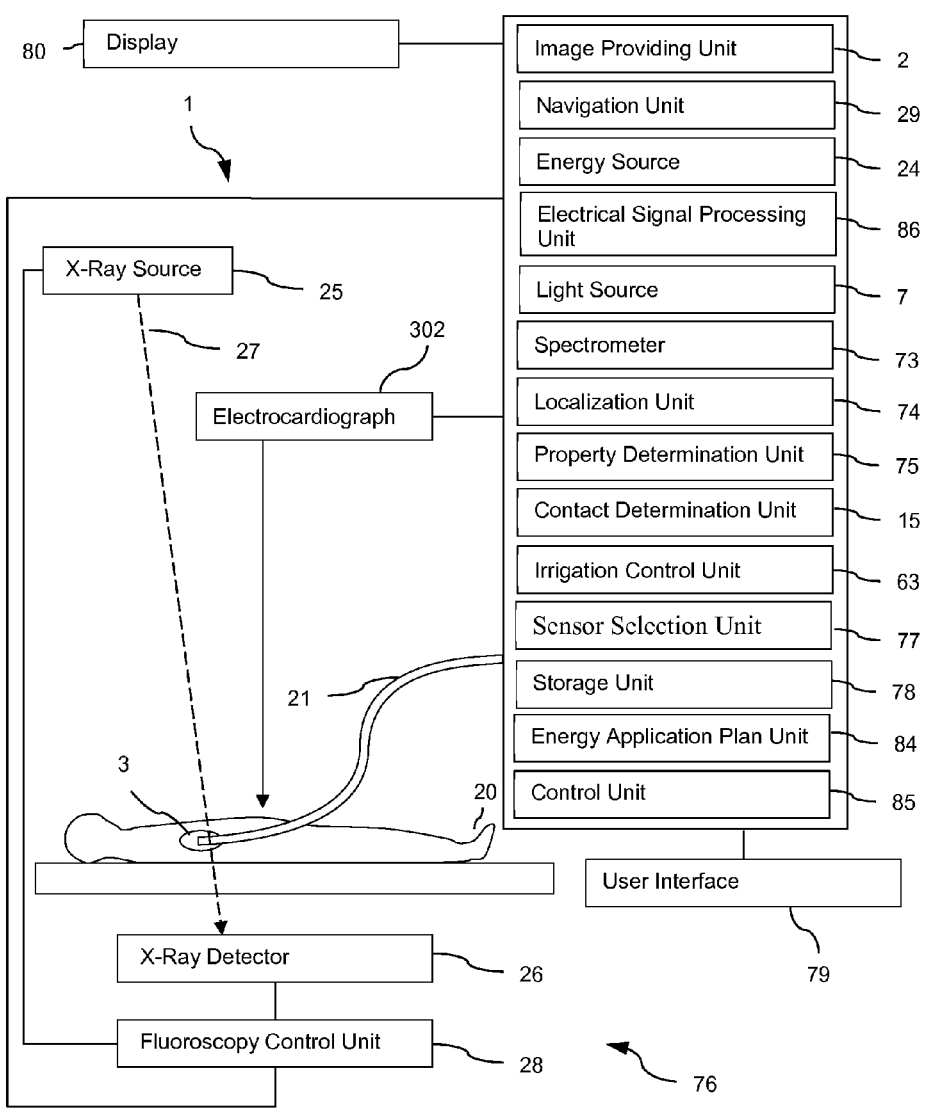
FIG. 1 shows schematically and exemplarily an embodiment of a property determination apparatus for determining a property of an object.

FIG. 1 shows schematically and exemplarily a property determination apparatus 1 for determining a property of an object. The property determination apparatus 1 comprises an image providing unit 2 for providing an image of the object 3 being, in this embodiment, a heart of a person 20. The property determination apparatus 1 further comprises a catheter 21 including optical sensors for generating optical sensing data for being indicative of an optical property of the object and ultrasound sensors for generating ultrasound sensing data being indicative of an ultrasound property of the object. The catheter allows the optical sensors and the ultrasound sensors to be introduced into the person 20, in order to determine a property of an inner wall of the heart 3. The property determination apparatus 1 further comprises an energy application element being, in this embodiment, an RF electrode for applying energy to the inner wall of the heart 3. Also the energy application element is integrated in the catheter 21. Thus, the catheter 21 can be introduced into the person 20, wherein energy can be applied to the inner wall of the heart 3 and a property of the inner wall of the heart 3 can be determined at the location at which energy is applied. The property can be determined before the energy is applied, while the energy is applied and/or after the energy has been applied. The energy is ablation energy for ablating cardiac tissue of the inner wall of the heart 3.

Figure 2:
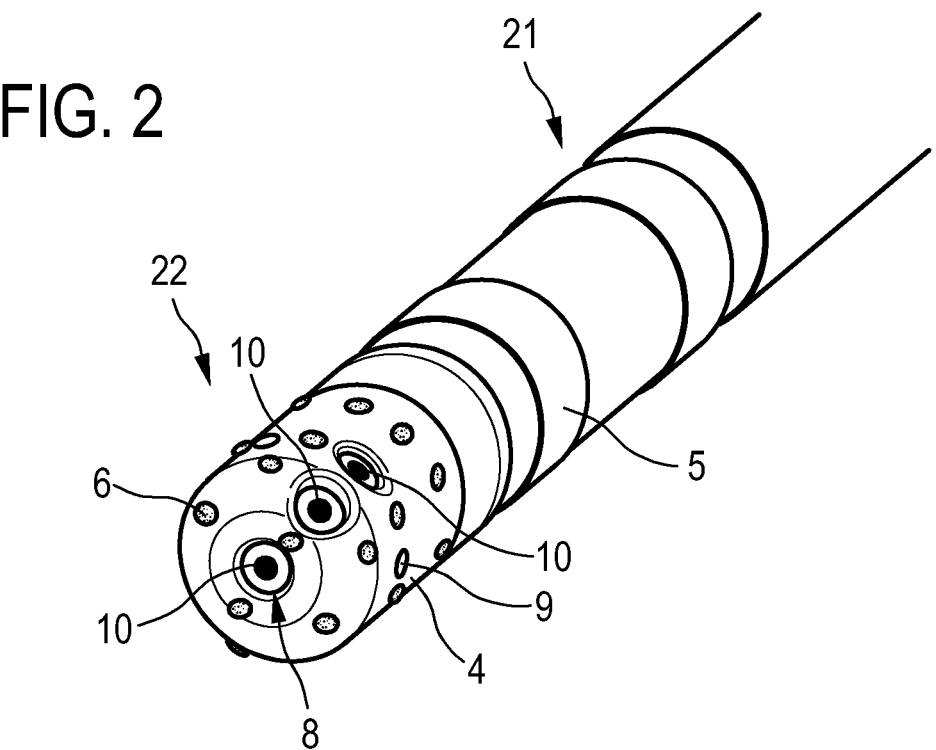
FIGS. 2 and 3 show schematically and exemplarily a distal end of a catheter of the property determination apparatus.
Figure 3:
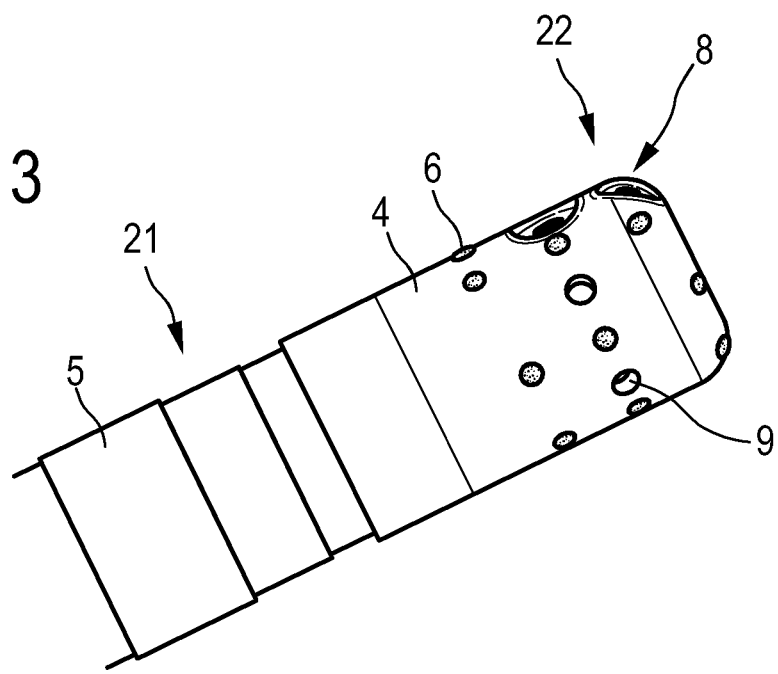

FIGS. 2 and 3 show schematically and exemplarily a distal end 22 of the catheter 21. In FIGS. 2 and 3, the ablation electrode 4 is a cap electrode which is connected to an energy source 24 via electrical connections for providing electrical energy, which can be applied to the inner wall of the heart 3. In this embodiment, the energy source 24, the electrical connections and the ablation electrode 4 are adapted to apply RF energy to the inner wall of the heart 3. The electrical connections are preferentially wires which are located within the catheter 21. The distal end 22 of the catheter 21 further comprises an electrode 5 for measuring local electrograms. The measured local electrograms can be used, for example, for generating and/or correcting an electroanatomical map and/or they can be shown on a display of the property determination apparatus for showing the local electrograms to a user, in particular, in order to allow the user to apply energy depending on the measured local electrograms. The electrode 5 is connected to an electrical signal processing unit 86 via electrical connections like electrical wires. The electrical signal processing unit 86 processes the local electrograms received from the electrode 5 and forwards the processed local electrograms to, for example, a display for showing the local electrograms on the display. In particular, the electrical signal processing unit 86 is preferentially adapted to digitize the local electrograms measured by the electrode 5 and to forward the digitized local electrograms to the display.

The ablation electrode 4 at the tip of the distal end 22 of the catheter 21 is preferentially a metallic part of the tip. Alternatively, the tip can be made of, for example, a polymer coated with electrically conductive material for providing the ablation electrode.

The optical sensor comprises preferentially light emitting means for illuminating the inner wall of the heart 3 by light and light receiving means for receiving light from the inner wall of the heart 3, wherein the optical sensor is adapted to generate optical sensing data depending on the received light. In this embodiment, the light emitting means and the light receiving means comprise several optical fibers 6 for illuminating the inner wall of the heart 3 at different positions and for receiving light from the inner wall of the heart 3. The several optical fibers for illuminating the inner wall of the heart 3 are connected to a light source 7 which comprises, for example, one or several lasers, wherein the several optical fibers 6 guide the light from the light source 7 to the inner wall of the heart 3. The several optical fibers for receiving light from the inner wall of the heart 3 are connected to a spectrometer 73 for generating one or several optical spectra of the inner wall of the heart 3.

The ablation electrode 4 comprises several irrigation openings 8 and 9 for allowing irrigation fluid, which is guided inside of the catheter 21, to leave the distal end 22 of the catheter 21 for irrigation purposes. The distal end 22 of the catheter 21 comprises a first kind of irrigation holes 8 being larger than a second kind of irrigation holes 9. In this embodiment, several ultrasound sensors, i.e. several ultrasound transducers 10, which are individually addressable, are physically confined to the interior of the ablation electrode 4 and arranged within the ablation electrode 4 such that each ultrasound transducer 10 can sense the inner wall of the heart 3 through one of the large irrigation openings 8.

Preferentially at a large irrigation opening 8 and/or at a small irrigation opening 9 two optical fibers are positioned across the respective irrigation opening at a distance of, for example, 1 mm. It is preferred that one of the two optical fibers is used for emitting light to the object and the other one is used for receiving light from the object, in order to measure an optical spectrum, which depends on the absorption and/or scattering properties of the underlying tissue. However, in other embodiments fibers can also be positioned according to any other spatial distribution on the distal end 22 of the catheter 21.

In an embodiment, the larger openings 8 are only used for allowing the ultrasound transducers 10 to sense the inner wall of the heart 3 through the respective larger opening 8, without allowing the irrigation fluid to leave the distal end 22 of the catheter 21 through the larger openings 8. The distal end 22 of the catheter 21 can have a diameter of 2.4 mm and the larger openings 8 can have a diameter of 0.5 mm. The optical fibers 6 can have a diameter of 0.25 mm and the distance between a pair of optical fibers, which are positioned across an opening, can be in the range of 1.0 to 2.0 mm, in particular, in the range of 1.2 to 1.8 mm.

The property determination apparatus 1 further comprises an irrigation control unit 63 being connected with the irrigation openings 8, 9 via an irrigation tube, in order to allow a user to control the irrigation of the cardiac tissue. If an ultrasound transducer 10 is arranged such that it can sense the inner wall of the heart 3 through the respective irrigation opening, the contact between the ultrasound transducer and the cardiac tissue is mediated by the irrigation fluid, in particular, if the space within the ablation electrode 4 is fluidly connected to the irrigation tube. If an opening, to which an ultrasound transducer can sense the inner wall of the heart, is not used for irrigation purposes, the opening can be closed by a window. In this case, the contact between the ultrasound transducer and the cardiac tissue can be mediated by an acoustically transparent material of the window like polymethylpentene or parylene.

The image providing unit 2 is preferentially adapted to provide an electroanatomical map of the heart 3. In this embodiment, the image providing unit 2 is a storing unit in which the electroanatomical map is stored. The electroanatomical map can be generated by generating a three-dimensional image of the heart 3, for example, by using a computed tomography system, a magnetic resonance imaging system, a nuclear imaging system or an ultrasound imaging system or by impedance, magnetic, electromagnetic or optically based tracking of the position of the catheter tip, and by measuring the electrical property of the heart at different locations on a wall of the heart, wherein the measured electrical properties are visualized at the respective locations in the three-dimensional image of the heart.

For example, the electroanatomical map can be an activation map reflecting the activation sequence of the anatomical substrate. From this activation map conduction patterns can be derived revealing, for example, zones of late activation or reentrant waves. The information from the activation map can be used to identify ablation targets to which energy should be applied.

The property determination apparatus 1 further comprises a localization unit 76, 74 for localizing the ablation electrode 4. The localization unit comprises an X-ray fluoroscopy system 76 with an X-ray source 25 and an X-ray detector 26. The X-ray source 25 emits an X-ray beam 27 which traverses the heart 3 including the distal end 22 of the catheter 21. The X-ray beam, which has traversed the heart 3, is detected by the X-ray detector 26. The X-ray detector 26 generates electrical signals depending on the detected X-ray beam and the electrical signals are used by a fluoroscopy control unit 28 for generating an X-ray projection image. The fluoroscopy control unit 28 is also adapted to control the X-ray source 25 and the X-ray detector 26. The X-ray source 25 and the X-ray detector 26 can be adapted to be rotatable around the patient 20 for allowing the X-ray fluoroscopy system 76 to generate X-ray projection images in different directions. The X-ray fluoroscopy system is, for example, a computed tomography fluoroscopy system or a C-arm fluoroscopy system. The X-ray projection images are provided to a position determination unit 74 for determining the position of the ablation electrode 4 within the heart 3. For determining the position of the ablation electrode 4 within the heart 3 based on the provided X-ray projection images known position determining methods can be used. For example, the ablation electrode can be recognized in the different X-ray projection images, which allows the position determination unit 74 to determine the paths of the X-rays which have caused the respective projection of the ablation electrode 4. The position determination unit 74 can be adapted to determine the position of the ablation electrode 4 within the heart 3 from the intersection of these paths. Or, a three-dimensional image of the ablation electrode 4 within the heart 3 can be generated from the X-ray projection images, for example, by using a backprojection algorithm, wherein the position determination unit 74 can be adapted to determine the position of the ablation electrode 4 within the heart 3 by recognizing the ablation electrode 4 within the heart 3 in the generated three-dimensional image. The position determination unit 74 can also be adapted to determine the orientation of the catheter, in particular, of the ablation electrode 4.

In other embodiments, the localization unit can comprise other means like a magnetic resonance imaging system or location sensors, for example, for magnetic and/or impedance based tracking at the distal end of the catheter for determining the position and optionally also the orientation of the ablation electrode 4 within the heart 3, in particular, for example, within an electroanatomical map of the heart. In further embodiments, the localization unit comprises sensors for optical shape sensing, for example, based on fiber bragg gratings or Rayleigh scattering.

The property determination apparatus 1 further comprises a property determination unit 75 for determining a property of the inner wall of the heart 3 based on the optical sensing data and the ultrasound sensing data. In particular, the property determination unit 75 is adapted to determine a property of the object depending on the optical spectra determined by the optical sensor. In this embodiment, the property determination unit 75 is adapted to determine a property of the surface of the inner wall of the heart 3 from the optical spectra. The optical spectra are indicative of the absorption and/or scattering properties of the surface and in particular of a surface layer, in which the light of the optical sensor can penetrate, and can therefore be used to determine scattering and/or absorption properties of the surface, in particular, of the surface layer, of the inner wall of the heart 3. In particular, the property determination unit 75 can determine properties of the inner wall of the heart 3 which influences the scattering and/or absorption properties of the inner wall of the heart 3. In this embodiment, the property determination unit 75 is adapted to determine whether cardiac tissue is ablated or non-ablated based on the optical spectra. The property determination unit 75 can further be adapted to determine the kind of tissue or the composition of the tissue sensed by the optical sensor.

The property determination unit 75 comprises a memory, in which optical spectra are stored, which are assigned to ablated cardiac tissue or to non-ablated cardiac tissue. The property determination unit 75 is adapted to compare the stored optical spectra with actually measured optical spectra, in order to determine whether the optically sensed cardiac tissue has been ablated or not. If the property determination unit 75 is further adapted to determine the kind of tissue or the composition of tissue, also optical spectra are stored in the memory, which are assigned to different kinds of tissue or to different possible elements of tissue, wherein the property determination unit 75 is adapted to determine the respective kind of tissue or the composition of the tissue by comparing the stored optical spectra with actually measured optical spectra.

For determining the optical spectra, the optical sensor can illuminate the inner wall of the heart 3 with light having different wavelengths, wherein the optical spectra are generated by using the spectrometer 73. Alternatively, the optical sensor can be adapted to illuminate the inner wall of the heart with different wavelengths temporally consecutively such that the optical fibers for receiving light from the inner wall of the heart receive light from substantially only one wavelength. Then, a spectrometer may not be needed, but a photodetector being sensitive to the respective wavelength. Thus, the output of the optical fibers, which have received the light from the inner wall of the heart can be detected by a photodiode for generating a detector signal and the detector signal can be processed in accordance with an algorithm, which will be described further below. Light is coupled out of the distal end 22 of the catheter 21 through at least one optical fiber and the wavelengths can be swept from, for example, 500 to 1600 nm. By spatially and temporally, i.e. wavelengths-dependent, multiplexing, optical spectra can be measured at multiple sites of the inner wall of the heart 3. Since the distal end 22 of the catheter 21 comprises several pairs of optical fibers, by using one catheter 21 several optical spectra can be determined at different sites of the inner wall of the heart 3 without moving the catheter between measurements of different optical spectra at different sites. In particular, optical spectra at different sites can be measured simultaneously with one catheter 21.

Although the measurement of optical spectra, which may be regarded as diffuse reflectance spectroscopy, is described above as being used to extract tissue properties, the optical sensor can also be adapted to perform other optical measurements for generating optical sensing data which are used by the property determination unit for determining tissue properties. For example, in other embodiments the optical sensor can be adapted to perform fluorescence measurements, diffuse optical tomography by employing a plurality of optical fibers, differential path length spectroscopy, or Raman spectroscopy for generating optical sensing data.

The property determination unit 75 can be adapted to determine optical tissue properties such as the scattering coefficient and/or the absorption coefficient of different tissue chromophores like hemoglobin, oxygenated hemoglobin, water, fat, et cetera. These optical tissue properties change during tissue ablation and are very different for healthy tissue compared to ablated tissue such that healthy tissue, in particular, healthy muscle tissue, can be discriminated from already ablated tissue or fat. In order to determine the scattering coefficients and/or the absorption coefficients of different tissue chromophores, the property determination unit 75 can be adapted to apply the spectral fitting procedure disclosed in "Estimation of lipid and water concentrations in scattering media with diffuse optical spectroscopy from 900 to 1600 nm" by Rami Nachabé et al., Journal of Biomedical Optics, Vol. 15(3), pages 1-10, May/June 2010, which is herewith incorporated by reference, to the measured optical spectra. The property determination unit can also be adapted to discriminate differences in optical spectra by making use of a principal components analysis as disclosed in, for example, "Partial Least-Squares Methods for Spectral Analyses. 1. Relation to Other Quantitative Calibration Methods and the Extraction of Qualitative Information" by David M. Haaland et al., Analytical Chemistry, vol. 60, no. 11, pages 1193 to 1202, June 1988, which is herewith incorporated by reference. The principal component analysis allows to classify differences in optical spectra and, thus, allows discrimination between tissues, in particular, discrimination between ablated and non-ablated tissue.

Figure 4:
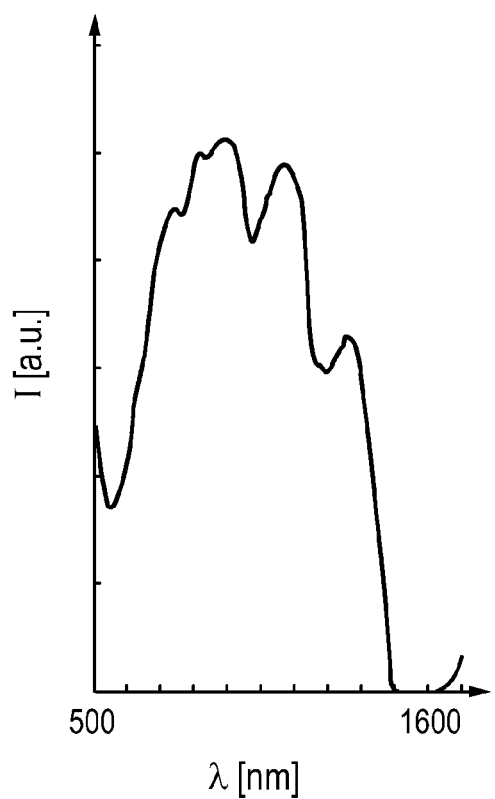
FIG. 4 shows exemplarily an optical spectrum of ablated cardiac tissue at a first location.
Figure 5:
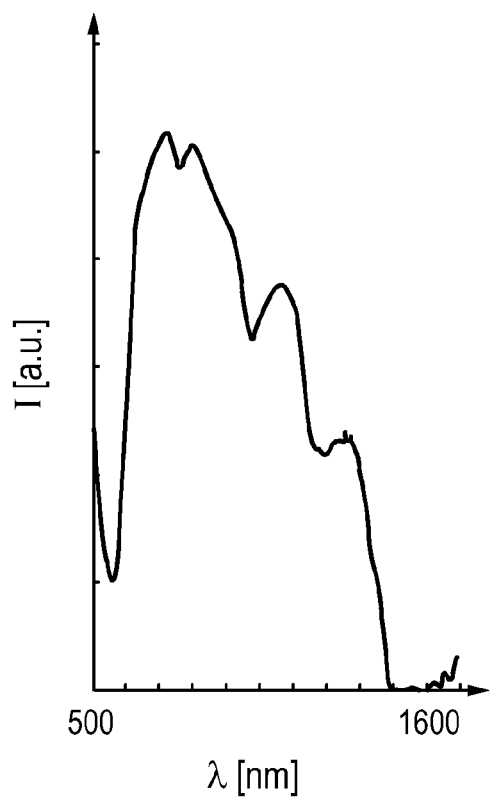
FIG. 5 shows exemplarily an optical spectrum of non-ablated cardiac tissue at a second location.
Figure 6:
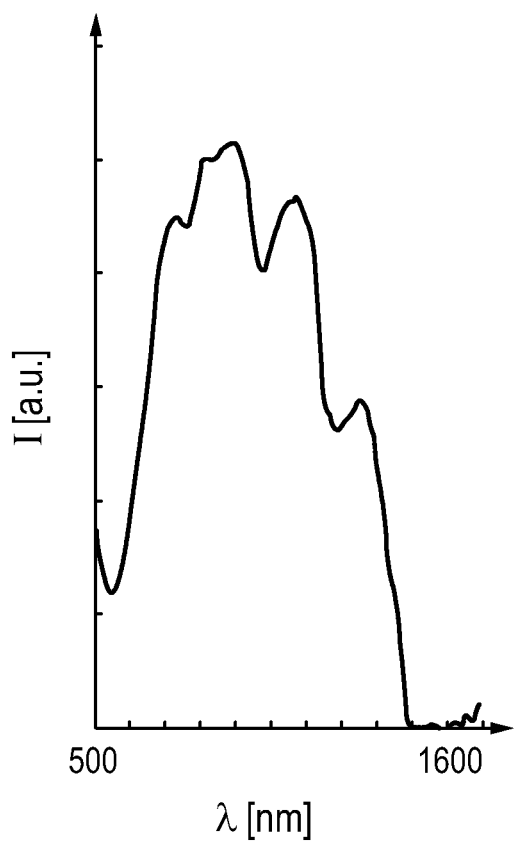
FIG. 6 shows exemplarily an optical spectrum of ablated tissue at a third location.

As already mentioned above, the property determination unit can also be adapted to distinguish between ablated tissue and non-ablated tissue by comparing an actually measured optical spectrum with stored optical spectra, which are assigned to ablated tissue or to non-ablated tissue. FIG. 4 shows schematically and exemplarily an optical spectrum of ablated tissue at a first location on the inner wall of a heart, FIG. 5 shows schematically and exemplarily an optical spectrum of non-ablated tissue at a second location, which is different to the first location, at the inner wall of the heart, and FIG. 6 shows schematically and exemplarily an optical spectrum of ablated tissue at a third location, which is different from the first location and the second location, on the inner wall of the heart. In these figures the vertical axis denotes the intensity I of the received light in arbitrary units and the horizontal axis denotes the wavelength λ in nanometer. As can be seen from these figures, the optical spectra of ablated tissue (FIGS. 4 and 6) are quite similar and different from the optical spectrum of non-ablated tissue shown in FIG. 5. Thus, by comparing the actually measured optical spectrum with stored optical spectra, which are assigned to ablated tissue or to non-ablated tissue, it can be determined whether at the location, at which the optical spectrum has actually been measured, the tissue is ablated or non-ablated.

In order to compare an actually measured optical spectrum with stored optical spectra, the property determination unit 75 is preferably adapted to use a similarity measure like a correlation or a sum of squared differences.

The property determination unit 75 can also be adapted to determine a degree of perfusion of the cardiac tissue from the optical sensing data, in particular, by using Laser Doppler Flowmetry (LDF). The determined degree of perfusion can be used to detect anomalies in the blood perfusion of tissue, in particular, of cardiac tissue, which can be addressed by segmenting scattered tissue, for example, after a myocardic infarct, by using ablation. If the property determination unit 75 is adapted to determine whether cardiac tissue is ablated or non-ablated by using LDF, the optical sensor comprises preferentially at least three optical fibers, one for illuminating the object and two for receiving light from the object, wherein the optical fiber for illuminating the object is placed at different distances from the two optical fibers for receiving the light from the object. Alternatively, the optical sensor can be adapted to use various wavelengths for illuminating the object. The LDF also enables diagnosing cardiac tissue by following a microcirculatory response to local heating, for example, during ablation. LDF enables quantification of blood perfusion of cardiac tissue down to 1 to 1.5 mm thickness that can be quantified in the number of red blood cells per 100 g of a certain tissue in mm/s. If the degree of perfusion has been determined by the property determination unit, the property determination unit can determine whether the tissue is ablated or non-ablated by thresholding the determined degree of perfusion. A corresponding threshold can be determined by calibration measurements, wherein the degree of perfusion is determined, while it is known whether the sensed tissue is ablated or non-ablated. A more detailed description of LDF can be found in, for example, the article "Optical microcirculatory skin model: assessed by Monte Carlo simulations paired with in vivo laser Doppler flowmetry" by Ingemar Fredriksson et al., Journal of Biomedical Optics, Vol. 13(1), pages 1 to 12, January/February 2008, which is herewith incorporated by reference.

The ablation energy is preferentially applied to the inner wall of the heart along a line, wherein the property determination unit 75 is preferably adapted to determine whether the ablation energy has been applied continuously along the line depending on the optical spectra. Preferentially, the optical sensor is adapted to generate the optical spectra at several positions along the line, in order to determine whether ablation energy had been applied continuously along the line depending on the generated optical spectra. For example, the distal end 22 of the catheter 21 can be moved continuously along the line, in order to measure optical spectra along this line. The property determination unit is preferably adapted to determine whether the cardiac tissue is ablated or non-ablated at the different positions along the line depending on the optical spectra measured at the different positions along the line, in order to determine whether the inner wall of the heart has continuously been ablated along this line. If the property determination unit determines a gap in the line, this gap can be reported to a user, in order to allow the user to ablate the inner wall of the heart in this gap for closing the line.

The property determination 75 is further adapted to determine a depth influence value being indicative of a depth to which the inner wall of a heart has been ablated from the ultrasound sensing data. The depth influence value is, for example, a lesion depth or a degree of transmurality with respect to the wall of the heart. The ablation electrode 4 can be controlled depending on the depth influence value, in particular, depending on the development of a lesion, which is defined by the lesion depth and caused by the ablation electrode 4. Thus, local lesion progression can be determined and the ablation electrode can be controlled based on the determined local lesion progression.

In order to determine the degree of transmurality, the property determination unit 75 is adapted to determine the thickness of the inner wall of the heart at the location at which the ablation electrode 4 applies energy from the ultrasound signal, wherein the degree of transmurality is determined based on the lesion depth and the thickness of the inner wall of the heart.

The ultrasound sensing data are an ultrasound signal representing ultrasound reflection properties of the inner wall of the heart at different depths, wherein the property determination unit 75 is adapted to determine a discontinuity of the ultrasound signal and to determine the lesion depth as the depth of the ultrasound signal at which the discontinuity occurs. The ultrasound signal preferentially also represents the ultrasound reflection properties at different times, i.e. the ultrasound signal is preferably an M-mode image, thereby allowing determining the lesion depth at different times, in particular, in realtime. This allows controlling the ablation electrode 4 in realtime depending on the lesion depth, in particular, such that an overtreatment like an overheating and an undertreatment are prevented.

The determination of the lesion depth and of the object wall thickness from the ultrasound signal will in the following exemplarily be described.

Figure 7:
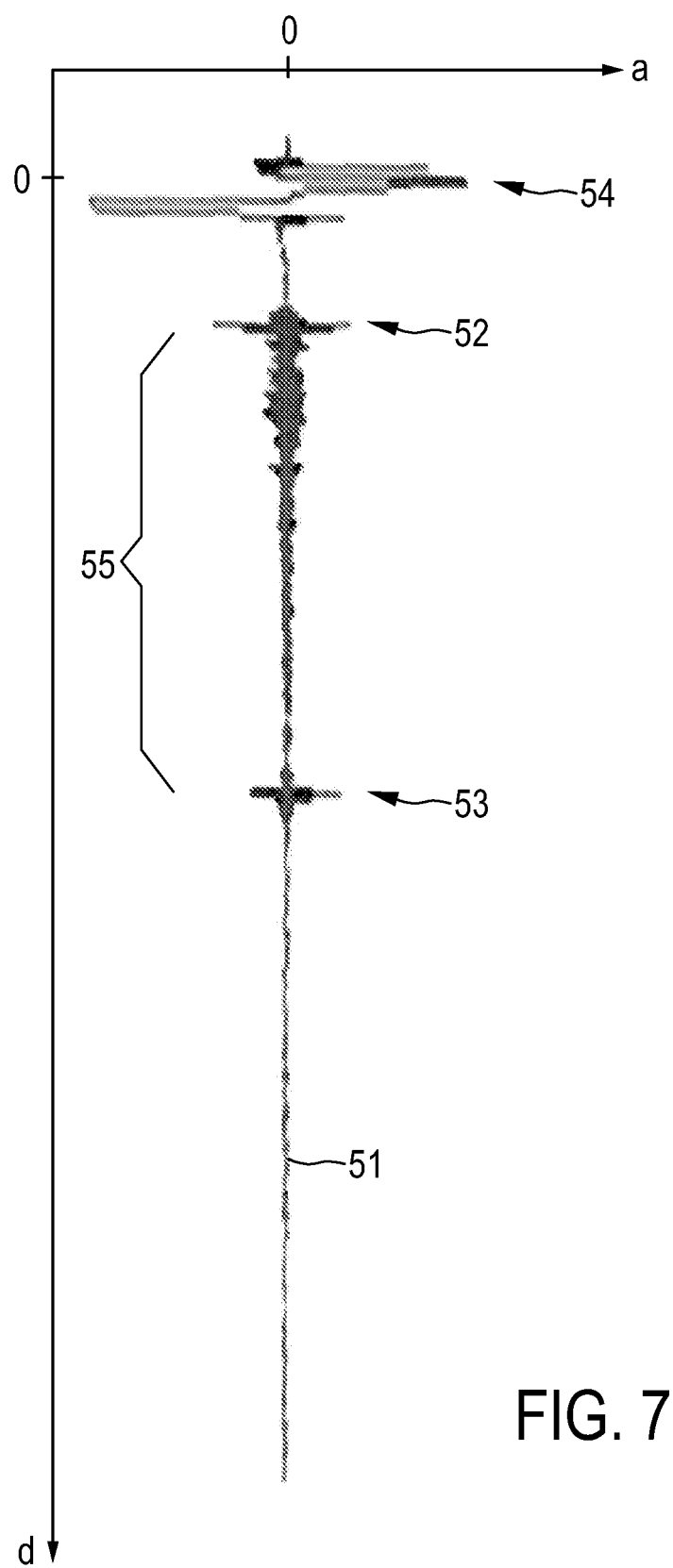
FIG. 7 shows schematically and exemplarily a representation of echo series produced by reflections of an ultrasound pulse at cardiac tissue.

If an ultrasound pulse is sent out to the object, the ultrasound pulse is reflected at different depths such that echo signals are received by the respective ultrasound element, i.e. ultrasound transducer 10. The echo signals, which are generated by reflection of the ultrasound pulse at different depths within the object, form an echo series. An echo series 51 is schematically and exemplarily shown in FIG. 7. By considering the speed of sound and the time, at which an echo is recorded after the ultrasound pulse has been sent out to the object, the echo series can be translated into a dependence of an ultrasound reflection property of the object on the depths within the object. In FIG. 7, the amplitude a of the echo series in arbitrary units, which corresponds to the ultrasound reflection property, is shown depending on the depth d in arbitrary units that corresponds to the time, at which the respective echo has been received after the pulse has been sent out into the object.

In this embodiment, the object is a heart, wherein the ultrasound pulse is sent out into the tissue of an inner wall of the heart. In FIG. 7, the regions of the echo series 51 denoted by 52 and 53, correspond to front and back surfaces of the heart wall. The region 54 is directly generated by the ultrasound pulse. Thus, in a strict sense, the echo series is the graph shown in FIG. 7 without region 54.

The echo series 51 shown in FIG. 7 allows determining the position of the front and back surfaces 52, 53 with respect to the position of an ultrasound element that emits the ultrasound pulse and receives the echoes. The first measured amplitude in the region 54 marks the position of the ultrasound element. Region 54 is followed by a region comprising an amplitude being substantially zero and after a while the amplitude increases again in region 52 marking the first reflection at the object, i.e. marking the front surface of the object. A region 55 comprising smaller amplitudes that correspond to reflections within the tissue of the heart wall follows, and then in the region 53 the amplitude increases again significantly thereby marking the back surface of the heart wall. Thus, the echo series 51 allows determining the positions of the front and back surfaces based on the regions 52 and 53 and, thus, determining the local object wall thickness as the difference between the positions of the front and back surfaces. The region 55 in between is used for determining the lesion depth as will be explained further below.

The position of the increasing amplitude in region 52 after a region comprising an amplitude value being substantially zero can be determined as the position of the front surface of the object. Then, the amplitude substantially decreases in region 55 and the position of the next significant increase of the amplitude (region 53) is determined as the position of the back surface of the heart wall. In other words, after the ring down of the ultrasound element in region 54 a "quiet period" ensues. This quiet period is subsequently terminated by a reflection in region 52 that is associated to the front surface. After this reflection in the region 52 a period 55 occurs that is marked by fast and small temperature changes in the ultrasound intensity. In particular, the envelope of the signal in the period 55 tends to have an exponential decrease in intensity. At the end of the period 55 again a strong reflection is observed in the region 53 that is associated to the back surface. Threshold values can be predefined, in particular relative threshold values can be predefined, wherein the front surface is detected, if a reflection after the "quiet period" exceeds the respective predefined threshold and wherein the back surface is detected, if at the end of period 55 the signal exceeds the respective threshold. The thresholds can be predefined by calibration measurements with walls having known front surface and back surface positions.

The echo series 51 exemplarily shown in FIG. 7 has been generated by an ultrasound pulse that was sent out into the object at a certain time. Several of these ultrasound pulses are sent out to the object at different times, thereby generating echo series at different times. These echo series, which are obtained from different ultrasound pulses at different times, and, thus, which belong to different times, form dynamic echo series. The ultrasound signal which depends on the received dynamic echo series represents therefore the ultrasound reflection properties of the object at different depths and at different times. Such an ultrasound signal is schematically and exemplarily shown in FIG. 8.

Figure 8:
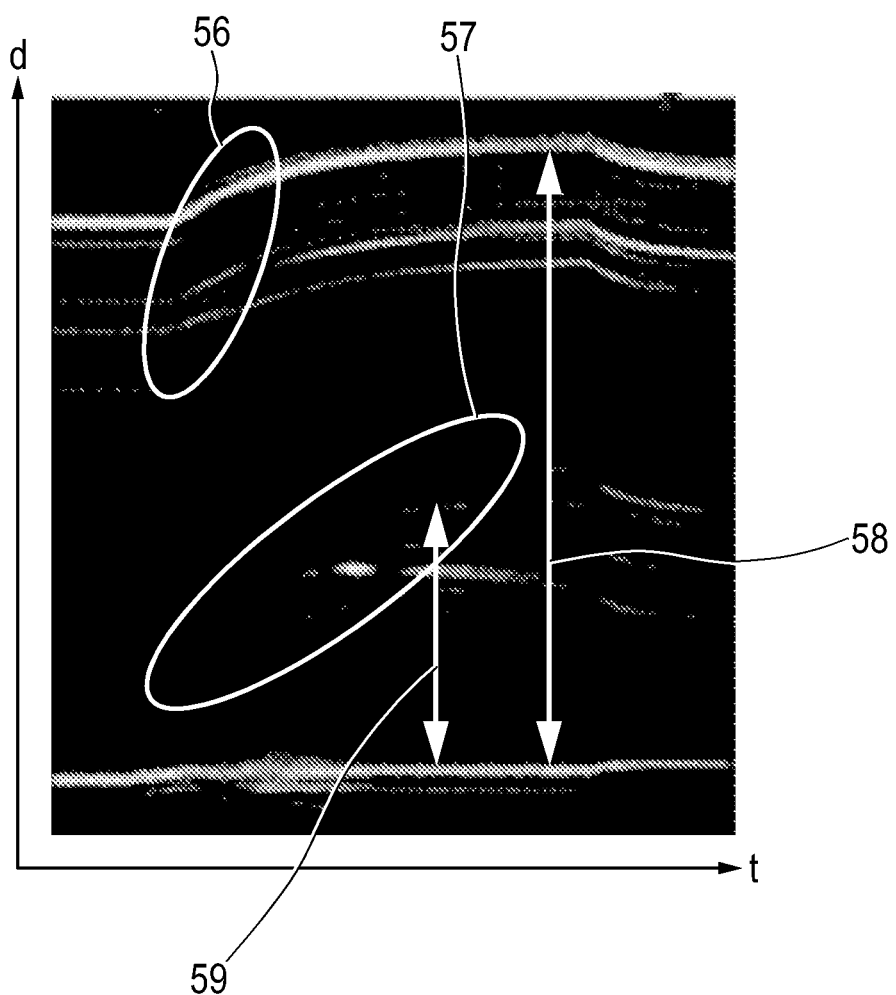
FIG. 8 shows schematically and exemplarily a two-dimensional representation of an ultrasound signal generated by an ultrasound transducer of the property determination apparatus.

In FIG. 8, different amplitudes of the ultrasound signal are indicated by different brightness, wherein a higher brightness corresponds to larger amplitude. The amplitude is shown depending on the depth d and the time t at which the respective echo series has been generated. The ultrasound signal shown in FIG. 8 forms an image that can be regarded as M-mode image.

By performing an ablation procedure, a lesion is generated in the heart wall, wherein the lesion depth is defined by the boundary of the lesion within the heart wall tissue.

The property determination unit is adapted to determine discontinuities in the ultrasound signal and to determine the lesion depth as a depth of the ultrasound signal at which the discontinuities occur. For example, in FIG. 8 in the first ellipse 56 only continuous variations of the ultrasound signal are present indicating a macroscopic tissue expansion of the heart wall tissue during applying ablation energy to the tissue. In the second ellipse 57 discontinuities in the variation of the ultrasound signal can be observed that indicate the lesion depth. Thus, FIG. 8 shows the progression of the lesion, i.e. the increasing lesion depth, in the second ellipse 57. Based on the observed discontinuities the lesion depth is determined as indicated exemplarily for a certain time by the second double arrow 59, whereas the first double arrow 58 indicates the thickness of the heart wall for a certain time. It should be noted that also the thickness of the heart wall changes with time during performing an ablation procedure due to a macroscopic tissue expansion as can be seen in FIG. 8.

For determining the lesion depth the property determination unit can be adapted to estimate time-resolved shifts, in particular, macroscopic shifts, in the ultrasound signal due to tissue expansion. In particular, the continuous variations of the ultrasound signal are detected and used for determining the shifts in the ultrasound signal due to tissue expansion for each time for which an ultrasound pulse has been sent out into the object and reflected by the object at different depths. Then, the property determination unit calculates a shift-compensated ultrasound signal to correct for the shift caused by tissue expansion during ablation. In particular, for different times the amplitude values shown in, for example, FIG. 8 are moved vertically in correspondence with the determined shift for compensating this shift caused by tissue expansion. Then, preferentially the property determination unit suppresses noise in the shift-compensated ultrasound signal using, for example, a Gaussian filter with, for example, $\sigma=25$. In an embodiment, the property determination unit is adapted to follow lines corresponding to a constant depth in the shift-compensated ultrasound signal with time, i.e. to follow horizontal lines in a representation of the shift-compensated ultrasound signal that corresponds to the representation shown in FIG. 8, until a disjunctive event occurs. The length of the horizontal lines before this disjunctive event occurs is determined by means of correlation statistics. Then, the property determination unit is adapted to assign ablated/non-ablated regions based on the determined lengths of connected stretches with a cut-off parameter that remains flexible. The cut-off parameter is, for example, 0.25 s. In particular, in a shift-compensated ultrasound image temporally adjacent pixels on a horizontal line are compared. If along a horizontal line a lesion boundary is not present, the pixels along the horizontal line tend to have roughly the same intensity and only slow variations may occur. In contrast, if a lesion boundary, i.e. the ablation lesion, reaches the horizontal line, the intensity of the pixels in this line change significantly. The depth associated with this significant change in the intensity defines the lesion depth. Preferentially, the property determination unit is adapted to determine stretches along a horizontal line comprising pixel values having substantially the same intensity. When an ablation front reaches a certain horizontal line, a significant decrease in the length of the stretches in this horizontal line is observed. If the length of the stretches is below a predefined threshold, the property determination unit determines the lesion depth as the depth associated to the location at which the length of the stretches is below this predefined threshold. This predefined threshold can be determined by calibration measurements, wherein ultrasound signals are generated by sending ultrasound pulses into the object having a known lesion depth. Also the similarity measure for determining whether adjacent pixel intensity values on a horizontal line are similar or not, i.e. whether two adjacent pixel value intensities on a horizontal line belong to the same stretch, can be determined by this calibration. For example, by calibration a relative threshold can be defined indicating the maximum relative difference in the pixel value intensities leading to the decision that these pixel value intensity values are regarded as being similar, i.e. two pixel value intensities are regarded as being similar if their relative difference is equal to or smaller than the maximum relative difference that is preferentially determined by calibration. In an embodiment, stretches having a length larger than 0.25 s, further preferred larger than 0.5 s and even further preferred larger than 1 s, are regarded as indicating that the ablation has not yet occurred at the depth corresponding to the respective horizontal line.

In a further embodiment, the property determination unit is adapted to Fourier transform the shift-compensated ultrasound signal in which noise has been preferentially suppressed by using, for example, a Gaussian filter. The depth dimension is subdivided into different depth regions, wherein for each depth region each line of signal values defined by the same time is cross correlated with its temporally preceding line of signal values which belong to the same preceding time. Thus, for the respective depth region a number of cross correlation lines is determined. The subdivision of the depth dimension in different depth regions corresponds to a sub division in a vertical direction in the M-mode image shown, for example, in FIG. 8. For example, the vertical lines can be subdivided into about 1000 depth regions. The number of depth regions can be predefined or can be selected automatically or by a user, for example, depending on the thickness of tissue to be examined or the ultrasound frequency. Preferentially, for very thin arterial tissue having a sub-millimeter thickness the number of depth regions is smaller than 1000 and for very thick ventricular tissue having a thickness being larger than 20 mm the number of depth regions is larger than 1000.

The cross correlation lines of the respective depth region are averaged. This averaging is preferentially performed by applying an average filter to the cross correlation lines of the respective depth region. The average filter has, for example, a filter width of eleven lines. However, the average filter can also have a wider or narrower filter width. Moreover, in this embodiment, the property determination unit is adapted to apply an inverse Fourier transformation on the averaged cross correlation lines of the different depth regions and to determine peaks within the depth regions of the inversely Fourier transformed cross correlation lines. Thus, preferentially, for each depth region and for each time a peak of the cross correlation line is determined.

The property determination unit can be adapted to determine the depth position of the peak within the respective depth region by cutting the peak out of the respective cross correlation line and by fitting a parabola to the cut out peak. The maximum of the fitted parabola defines the depth position of the peak within the respective depth region at the respective time.

The property determination unit can further be adapted to determine for each depth region and for each time a shift value from the depth position of the peak within the respective depth region at the respective time. Since the peak is a peak of a cross correlation line, the depth position of the peak within the respective depth region is indicative of the shift between the two lines of signal values within the depth region, which have been cross correlated for determining the respective cross correlation line. The property determination unit can be adapted to determine the depth position of the peak within the respective depth region as the shift value or the property determination unit can be adapted to perform further steps for determining a shift value depending on the respective depth position of the peak within the respective depth region. For example, predefined assignments between depth positions of the peak within a depth region and shift values can be stored in the property determination unit and used for determining a shift value depending on the determined depth position of the respective peak within the respective depth region. These assignments can be determined, for example, by calibration.

The property determination unit can be adapted to determine a lesion depth and an ablation time depending on the shift values which have been determined for different depth regions and at the different times. For determining the lesion depth and the ablation time a thresholding is preferentially performed on the determined shift values. If a shift value is larger than a predefined shift threshold, the corresponding depth region and time are regarded as a lesion depth, at which the ablation process occurs, and as ablation time, respectively. This shift threshold is predefined and stored in the property determination unit and can be determined by calibration measurements.

Preferentially, the property determination unit is adapted to apply a noise reduction filter being a high-frequency filter on the ultrasound signal. For example, the high-frequency filter can be a Hilbert filter. However, the high-frequency filter can also be another filter like a filter using a band pass cut-off frequency or a filter using envelope detection. FIG. 8 shows an ultrasound signal on which a Hilbert filter has been applied.

For interpreting the ultrasound signal shown in FIG. 8, the graph can be separated into various parts and re-plotted as exemplarily shown in FIGS. 9 to 13.

Figure 9:
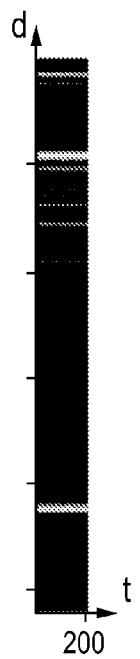
FIGS. 9 to 13 show schematically and exemplarily representations of different parts of an ultrasound signal that correspond to different time periods before, during and after an ablation procedure.

In FIG. 9, the ablation procedure is not applied, for example, an RF frequency ablation electrode 4 is not operated. Thus, the ultrasound signal is constant with respect to variations in time, i.e. the reflection properties of the tissue of the heart wall are substantially not modified.

Figure 10:
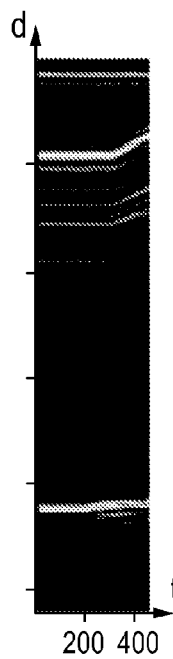
Figure 11:
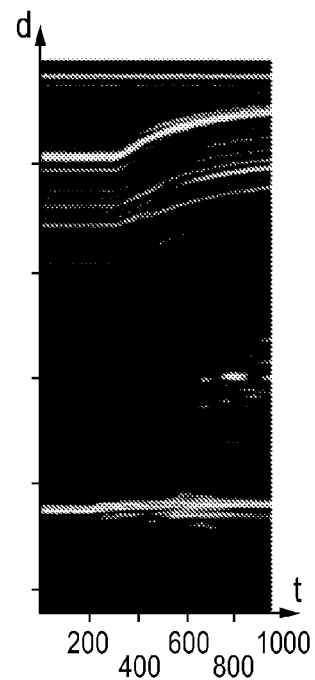
Figure 12:
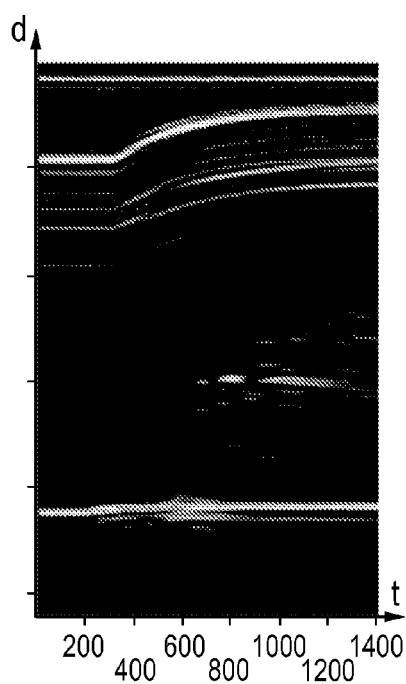
Figure 13:
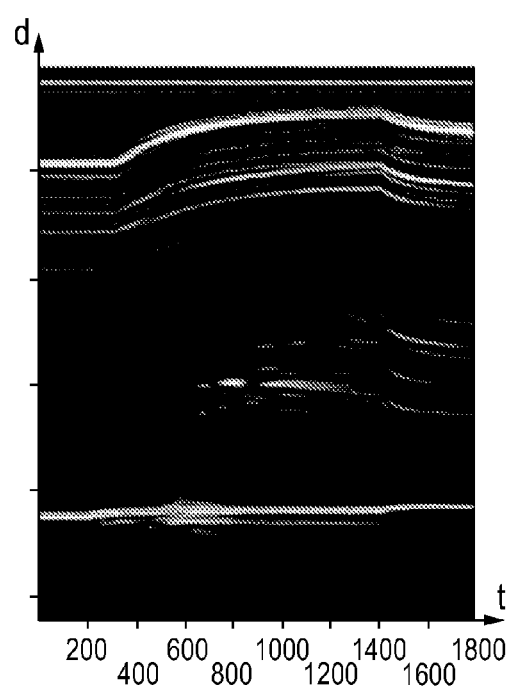

Upon ablation, the part of the tissue to which energy is applied heats up and the ultrasound signal originating from that region starts to change (FIG. 10). It can also be observed that the heated region expands due to the thermal load and pushes the yet not heated part of the tissue in a direction that corresponds to a direction from the bottom to the top in FIGS. 8 to 13. In FIGS. 11 and 12 it is shown how the ultrasound signal changes if the ablation procedure continues. In FIG. 13, the ablation procedure has been stopped, i.e. the heat source (ablation element) has been switched off, resulting in shrinkage by cooling down and a shift of the stripes that correspond to the back surface of the heart tissue wall back towards the original position before ablation. The part of the tissue which was not treated and where no dynamical signal changes are observed preserves its thickness and just shifts its position.

Figure 14:
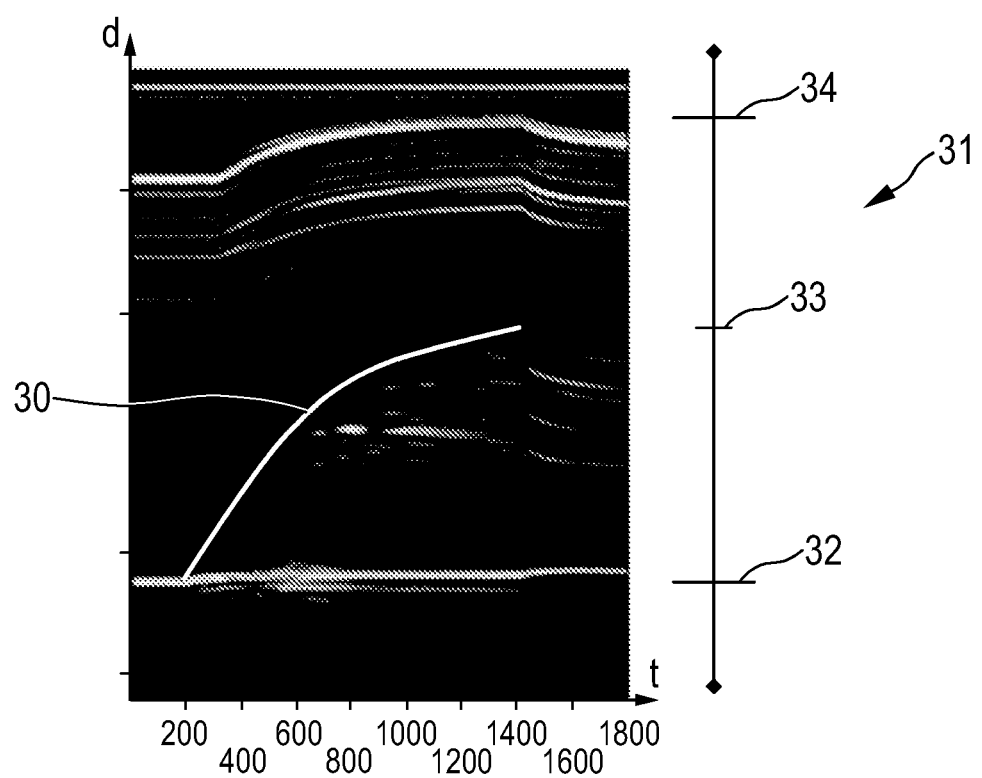
FIG. 14 shows schematically and exemplarily a determined lesion depth and a two-dimensional representation of the ultrasound signal.

FIG. 14 shows schematically and exemplarily a line 30 indicating the lesion depth determined by the property determination unit at different times, thereby indicating the progression of ablation. FIG. 14 further shows a slide bar 31 indicating the positions of the front surface and the back surface of the heart tissue wall by lines 32 and 34, respectively, and the lesion depth by line 33 for a certain time. In FIG. 14, the slide bar 31 is shown for the moment when the ablation stops. FIG. 14 can be shown on a display 10 for visualizing the progression in ablation.

In FIGS. 8 to 14 the ultrasound signal for a constant time, i.e. the ultrasound signal along a vertical line in these figures, could be regarded as A-line of the ultrasound signal. In FIGS. 8 to 14 the ultrasound signal is shown depending on the depth d within the heart tissue wall and the time t in arbitrary units.

The ultrasound elements can be single probes which allow visualization in one direction, or they can be probes which allow two-dimensional and/or three-dimensional scanning such as a phased array, a rocker probe, a micro-machined ultrasound transducer (MUT) array, et cetera.

The property determination apparatus 1 further comprises a contact determination unit 15 for determining whether the ablation electrode 4 is in contact with the inner wall of the heart 3 based on the ultrasound sensing data. This allows controlling the application of energy depending on whether the ablation electrode 4 is in contact with the inner wall of the heart 3 or not. In particular, the application of energy can be controlled such that energy is applied to the inner wall of the heart 3 only, if the ablation electrode 4 is in contact with the inner wall of the heart 3, thereby improving the quality of applying energy to the inner wall of the heart 3.

For example, it can be verified whether the object is in contact with the ablation electrode 4 based on the position of the surface of the object with respect to the respective ultrasound element 10, which can be determined from the ultrasound signal, and based on a known spatial relationship between the ablation electrode 4 and the respective ultrasound element 10. This spatial relationship is known, because it is known at which position and in which orientation the respective ultrasound element is arranged within the ablation electrode 4 or because, in an embodiment, a part of the ablation electrode is a little bit hanging over the ultrasound element such that a part of the ultrasound waves is reflected by the respective ablation electrode, for example, two to five percent of the ultrasound intensity can be reflected by a part of the ablation electrode. In the latter case, the ablation electrode is visible in the ultrasound signal and the thus known position of the ablation electrode can be used together with the determined position of the surface of the object for determining whether the ablation electrode is in contact with the object or not. It is also possible to determine whether the respective ablation element is in contact with the object depending on the ultrasound pattern of, for example, an A-line or an M-mode image. For example, if the ultrasound signal is not stable, it can be concluded that the contact between the object and the ablation electrode is not good enough or that there is no contact at all. In this case, the distal end of the catheter is preferentially forced towards the object for increasing the contact force.

Referring again to FIGS. 2 and 3, the ultrasound transducers 10 are arranged within the distal end 22 of the catheter 21 such that they can sense the object in different sensing directions. The property determination apparatus 1 further comprises an ultrasound sensor selection unit 77 for selecting an ultrasound transducer among the several ultrasound transducers 10 within the distal end 22 of the catheter 21 depending on the generated optical sensing data, i.e. the optical spectra, wherein the property determination unit 75 is adapted to determine a property like the lesion depth and/or the degree of transmurality depending on the ultrasound sensing data of the selected ultrasound transducer. The ultrasound sensor selection unit 77 is adapted to determine the orientations of the sensing directions relative to the inner wall of the heart 3 from the optical sensing data and to select an ultrasound transducer based on the determined orientations. The positions and orientations of the optical fibers 6 and of the ultrasound transducers with respect to the distal end 22 of the catheter 21 are known such that the ultrasound sensor selection unit is preferentially adapted to determine the orientation of the distal end 22 of the catheter 21 with respect to the inner wall of the heart 3 based on the optical sensing data and the known spatial relationship between the optical fibers 6 and the distal end 22 of the catheter 21 and to select an ultrasound transducer based on the determined orientation of the distal end 22 of the catheter 21 with respect to the inner wall of the heart 3 and the known spatial relationship between the ultrasound transducers 10 and the distal end 22 of the catheter 21. The ultrasound sensor selection unit 77 is preferentially adapted to select the ultrasound transducer of which the sensing direction is most perpendicular to the surface of the inner wall of the heart 3 to which energy is applied or has been applied. The ultrasound sensing data of the selected ultrasound transducer is preferentially used to determine, for example, the lesion depth or the degree of transmurality.

Several optical fibers are distributed over the distal end 22 of the catheter 21 such that optical spectra can be measured in different directions. The ultrasound sensor selection unit 77 is preferentially adapted to determine optical sensor contact information being indicative of which optical fibers are in contact with the object, i.e. the inner wall of the heart 3, and to determine the orientation of the distal end 22 of the catheter 21 and, thus, of the sensing directions of the ultrasound transducers relative to the inner wall of the heart 3 depending on the optical sensor contact information and the spatial relationship between the several optical fibers and the distal end 22 of the catheter 21. If an end of an optical fiber is not in contact with the inner wall of the heart 3, irrigation fluid like saline and/or blood is present between the end of the optical fiber and the inner wall of the heart 3. The present irrigation fluid and/or present blood leads to an optical spectrum which is indicative of the present irrigation fluid and/or the present blood. Thus, by comparing the actually measured optical spectrum with stored optical spectra, which may be stored in a memory of the ultrasound sensor selection unit 77 and which may be assigned to, for example, irrigation fluid and/or blood, it can be determined whether irrigation fluid and/or blood is present between the end of the optical fiber and the inner wall of the heart 3, in order to determine whether the end of the optical fiber is in contact with the inner wall of the heart 3 or not. Since the spatial relationship between the ends of the optical fibers 6 with respect to the distal end 22 of the catheter 21 is known, the orientation of the distal end 22 of the catheter 21 can be determined based on this known spatial relationship and based on the positions of the ends of the optical fibers, which are in contact with the inner wall of the heart 3.

Figure 15:
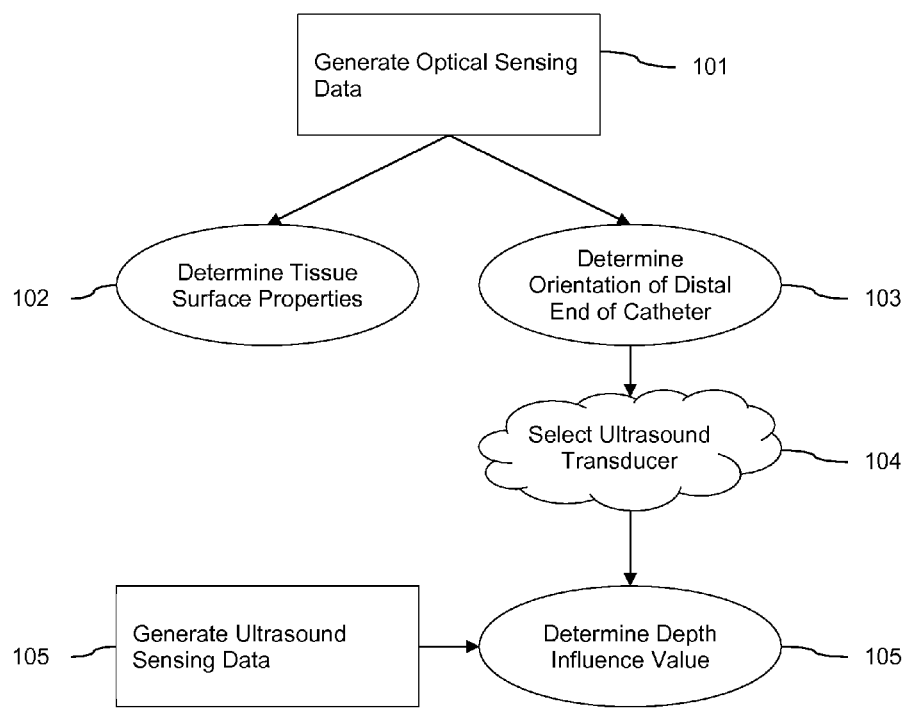
FIG. 15 shows a flowchart exemplarily illustrating an embodiment of a property determination method.

The information on the tip orientation, i.e. on the orientation of the distal end 22 of the catheter 21, based on optical measurements can therefore be used as an input for the processing of the ultrasound sensing data recorded with the multiple ultrasound transducers 10 in the distal end 22 of the catheter 21. This will in the following exemplarily be described with reference to a flowchart shown in FIG. 15.

In step 101, optical sensing data, i.e. optical spectra, are generated by sensing the inner wall of the heart 3 by using the optical fibers 6. In step 102, the property determination unit 75 determines tissue surface properties like whether the sensed tissue is ablated tissue or non-ablated tissue. Moreover, in step 103, the ultrasound sensor selection unit 77 determines the orientation of the distal end 22 of the catheter 21 and selects, in step 104, an ultrasound transducer having a sensing direction being most perpendicular to the inner wall of the heart 3 depending on the tip orientation determined in step 103 and the known spatial relationship between the sensing directions of the ultrasound transducers 10 and the distal end 22 of the catheter 21. Alternatively, or in addition in step 104 the determined orientation of the distal end 22 of the catheter 21 can be shown to a user, in order to allow a user to modify the orientation of the distal end 22 of the catheter 21, wherein after this modification steps 101, 103 and 104 are performed again. In a further alternative, the orientation of the distal end 22 of the catheter 21 determined in step 103 can be used to automatically modify the orientation of the distal end 22 of the catheter 21 such that a sensing direction of an ultrasound transducer is as perpendicular as possible to the inner wall of the heart 3. In step 105, which is preferentially performed concurrently with step 101, ultrasound sensing data are generated by the ultrasound transducers 10. In step 106, the ultrasound sensing data, i.e. the ultrasound signal, of the selected ultrasound transducer is used for determining a depth influence value, in particular, for determining a lesion depth and/or a degree of transmurality.

Referring again to FIGS. 2 and 3, the optical fibers are adapted to illuminate the inner wall of the heart 3 in different directions, in particular, to illuminate the inner wall in a frontal direction and also in a sideward looking direction. Since the ability to bend optical fibers is limited, for illuminating the object in the sideward looking direction a mirror is formed in the material of the ablation electrode 4, in order to reflect the light from the respective optical fiber towards the respective side. For this purpose, light can for example be coupled out from an optical fiber in a certain angle by machining a slanted distal end on the respective optical fiber and by coating the surface at the slanted distal end with a metallic layer as schematically and exemplarily shown in FIG. 16.

Figure 16:
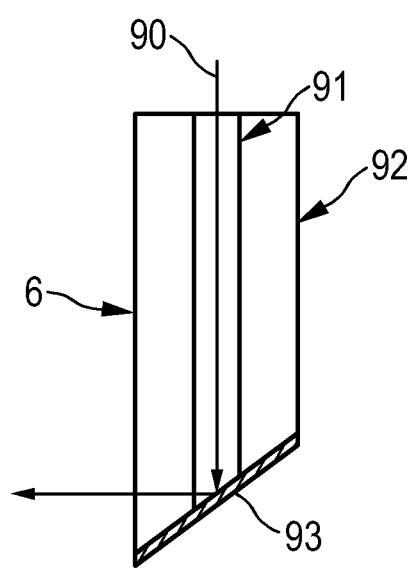
FIG. 16 shows schematically and exemplarily an optical fiber comprising a mirror for illuminating the object by light in a sideward looking direction.

In FIG. 16, an optical fiber 6 comprises a core 91 and a cladding 92. Moreover, on a slanted end surface of the optical fiber 6 a metallic coating is provided for forming a mirror 93. The metallic coating can be, for example, a layer of about 100 nm of silver on, for example, a chromium adhesion promoter layer of, for instance, about 5 nm. The light is guided along the light path 90 such that it is reflected by the mirror 93 in a sideward looking direction.

The energy application apparatus 1 further comprises a navigation unit 29 for allowing the catheter 21, in particular, the distal end 22 of the catheter 21, to be navigated to a desired location within the object. The navigation unit 29 can be adapted to allow a user to navigate the catheter 21 completely by hand or semi-automatically depending on a determined position and preferentially orientation of the distal end 22. The catheter 22 comprises build-in guiding means (not shown in FIG. 1), which can be controlled by the navigation unit 29. The catheter 21 can, for example, be steered and navigated by the use of steering wires in order to guide the distal end 22 to a desired location within the object.

The property determination apparatus 1 further comprises a display 80 for displaying at least one of the optical sensing data, the ultrasound sensing data and the determined property of the object 3. The energy is applied to the inner wall of the heart 3 at an energy application location on the wall, wherein the optical sensor is adapted to generate optical sensing data being indicative of an optical property of the cardiac tissue at the energy application location, i.e. to generate at least one optical spectrum at the energy application location, wherein the ultrasound sensor is adapted to generate ultrasound sensing data at the energy application location and wherein the property determination unit 75 is adapted to determine whether the cardiac tissue is ablated or non-ablated at the energy application location based on the optical sensing data and to determine the lesion depth and particularly the degree of transmurality at the energy application location based on the ultrasound sensing data. The property determination apparatus 1 further comprises a storage unit 78 for storing the optical sensing data, the ultrasound sensing data and the determined property, which have been measured and determined, respectively, for the respective energy application location. The image providing unit 2 is adapted to provide an image of the heart, for example, an electroanatomical map of the heart, wherein the display 80 is adapted to display 80 the energy application location on the image. The property determination apparatus 1 further comprises a user interface 79 for allowing a user to select the shown energy application location, wherein the display 80 is adapted to display 80 at least one of the optical sensing data, the ultrasound sensing data and the determined property, if the displayed energy application location has been selected by the user. This allows a user to study the optical sensing data, the ultrasound sensing data and/or the determined property of the object like the lesion depth and/or the degree of transmurality, which correspond to the selected energy application location. Also the determined orientation of the distal end 22 of the catheter 21 can be stored in the storage unit 78 and displayed, if the corresponding energy application location has been selected.

In a preferred workflow, the optical spectra are measured before energy is applied, i.e. before ablation starts, and at the end of ablation. The orientation of the distal end 22 of the catheter 21 can be determined during ablation and stored in the storage unit 78. Also the ultrasound sensing data can be measured during ablation and stored in the storage unit 78. The stored information is linked to a point tag representing the ablated spot, i.e. is linked to a tag on the display 80 representing the energy application location, wherein the tag is shown on, for example, an electroanatomical map or on an EP navigator, from the company Philips. Also further determined properties of the inner wall of the heart 3 at the respective energy application location can be stored and linked to the respective displayed tag. Preferentially, it is stored whether the cardiac tissue is ablated or non-ablated at the respective energy application location, wherein this information can be used to identify gaps in a lesion line, which is generated by applying ablation energy along a line and which should be closed.

The storing of spectral data of an ablated spot, which serves as a kind of fingerprint, can be used to find a more accurate reference point or starting point for consecutive ablations along a line given the inaccuracy of electroanatomical maps, which is up to 1 cm. In addition, the distal end 22 of the catheter 21 may be moved back to a previously ablated spot, for example, with redo procedures, based on the stored information.

Figure 17:
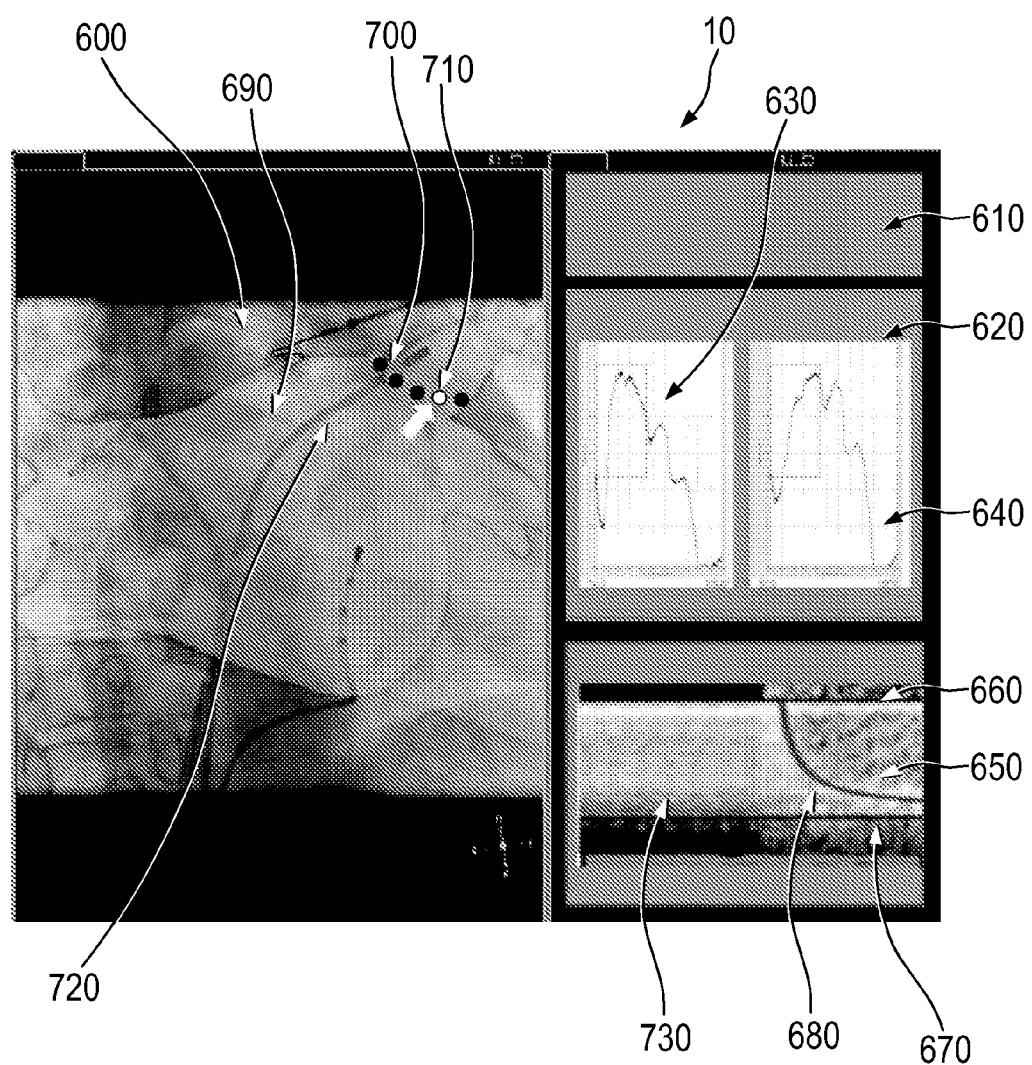
FIG. 17 shows schematically and exemplarily a display of the property determination apparatus.

FIG. 17 shows schematically and exemplarily the display 10 in more detail. The display 10 can comprise a first region 600, in which a representation 690 of the heart and several catheters 720 are shown. Moreover, several energy application locations are marked by using markers 700, wherein the marker 710 has been selected by the user. In a second region 610 of the display 10 energy application settings, in particular, ablation settings like the power and the duration of the applying power, can be shown. In a third region 620 of the display 10 a first optical spectrum 630 can be shown, which has been measured before the cardiac tissue was ablated at the selected energy application location 710, and a second optical spectrum 640 can be shown, which has been measured at the selected energy application location 710 after the ablation procedure has been performed. In a fourth region 650 of the display 10 an M-mode image 730 is shown, which has been measured at the selected energy application location 710. In the M-mode image 730 the front wall 660 and the back wall 670 of the heart wall and the lesion line 680 indicating the lesion depth are shown. In the fourth region 650 also the degree of transmurality can be indicated, for example, by providing a text which describes the degree of transmurality.

In the first region 600 of the display 10 a fluoroscopy image generated by the x-ray fluoroscopy system 76 and/or an electroanatomical map can be shown.

Figure 18:
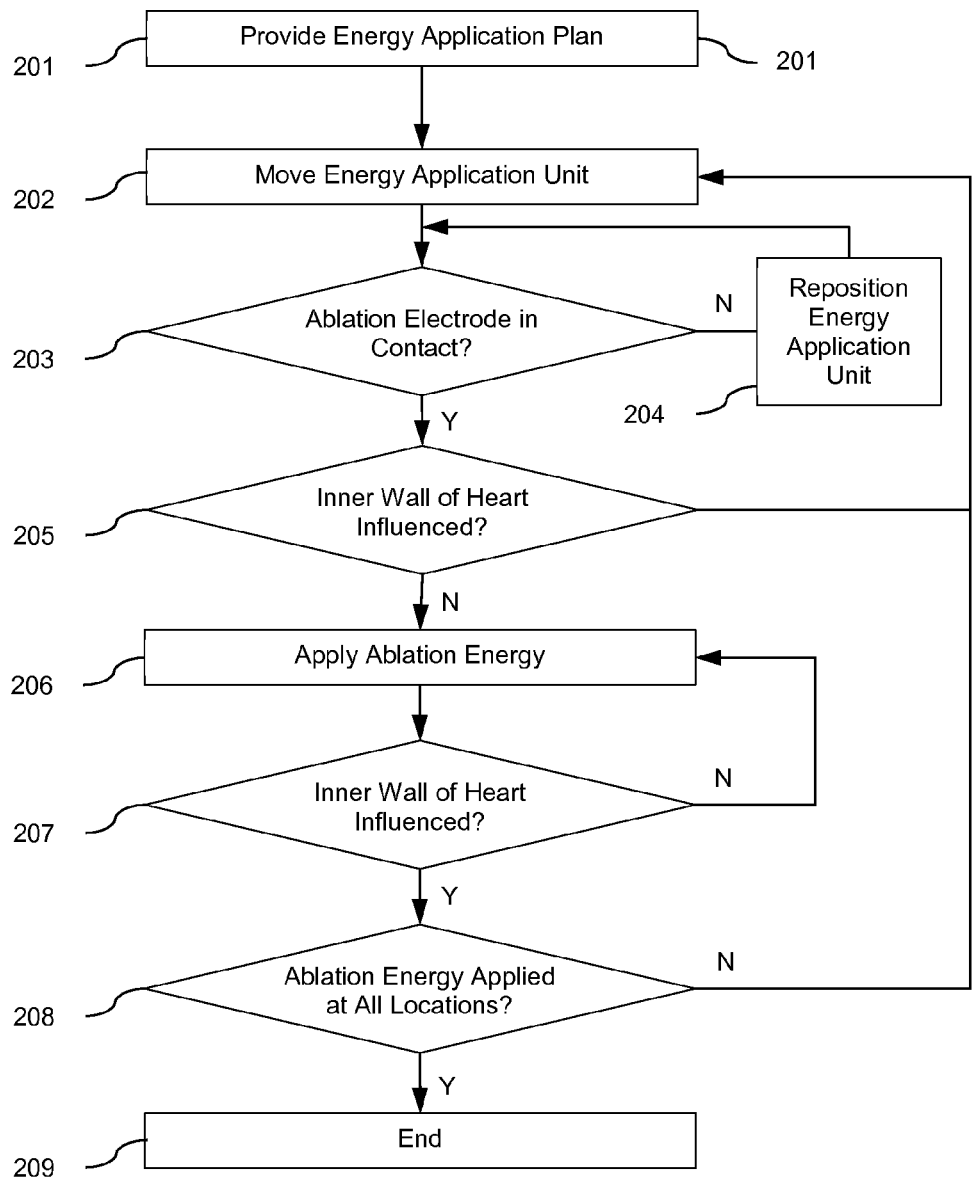
FIG. 18 shows a flow chart illustrating a further embodiment of a property determination method for determining a property of an object.

The property determination apparatus 1 further comprises an energy application plan providing unit 84 for providing an energy application plan comprising energy application locations at which energy is to be applied to the inner wall of the heart 3. In particular, the energy application plane defines energy application locations along a closed line, wherein the tissue along this line should continuously be ablated. The property determination apparatus 1 further comprises a control unit 85 for controlling the property determination apparatus in accordance with a property determination method which will in the following exemplarily be described with reference to a flowchart shown in FIG. 18. In step 201, an energy application plan comprising energy application locations at which energy is to be applied to the inner wall of the heart 3 is provided by the energy application plan providing unit 84. In step 202, the energy application element, i.e. the ablation electrode 4, the optical fibers 6 of the optical sensor and the ultrasound transducers 10 are moved to an energy application location, in particular, to a first energy application location, of the energy application plan by the navigation unit 29 which can also be regarded as a moving unit. The ablation electrode 4, the optical fibers 6 and the ultrasound transducers 10 are moved to the energy application location by moving the distal end 22 of the catheter 21 to the energy application location. Thus, only a single element, i.e. the distal end 22 of the catheter 21, has to be moved to the energy application location. In step 203, ultrasound sensing data are generated at the energy application location by at least one of the ultrasound transducers 10 and it is determined whether the ablation electrode 4 is in contact with the inner wall of the heart 3 at the energy application location based on the ultrasound sensing data by the contact determination unit 15. If the ablation electrode 4 is not in contact with the inner wall of the heart 3, the position of the ablation electrode is modified by the navigation unit 29 in step 204, in particular, the ablation electrode 4 is moved further towards the inner wall of the heart 3. After this movement of the ablation electrode 4 towards the inner wall of the heart 3, ultrasound sensing data are again generated and it is again determined whether the ablation electrode 4 is in contact with the inner wall of the heart 3. Steps 203 and 204 are repeated, until the ablation electrode 4 is in contact with the inner wall of the heart 3.

Then, in step 205, optical sensing data are generated at the energy application location by the optical sensor and the property determination unit 75 determines whether the inner wall of the heart 3 has already been influenced by energy at the energy application location depending on the generated optical sensing data. If the inner wall of the heart 3 has already been influenced by energy at the energy application, the method continues with step 202 for moving the ablation electrode 4, the optical fibers 6 and the ultrasound transducers 10 to a next energy application location of the energy application plan. If the inner wall of the heart 3 has not been influenced by energy at the energy application location, i.e. if the inner wall of the heart 3 has not already been ablated at the energy application location, ablation energy is applied to the inner wall of the heart 3 at the energy application location in step 206 by the ablation electrode 4. In step 207, ultrasound sensing data are generated at the energy application by at least one of the ultrasound transducer 10. Preferentially, the optical sensing data generated in step 205 are used for determining the orientation of the distal end 22 of the catheter 21 with respect to the inner wall of the heart 3, wherein the determined orientation is used to select one ultrasound transducer having a sensing direction being most perpendicular to the inner wall of the heart 3. Moreover, in step 207 the property determination unit 75 determines whether the inner wall of the heart 3 has been influenced by energy to a predefined degree, in particular, if the inner wall of the heart 3 is transmural, at the energy application location by depending on the ultrasound sensing data, wherein steps 206 and 207 are repeated, until the inner wall of the heart 3 has been influenced by energy to the predefined degree at the energy application location. In step 208, it is determined whether energy has been applied at all energy application locations of the energy application plan, wherein, if energy has not been applied to all energy application locations of the energy application plan, the method continues with step 202 for moving the distal end 22 of the catheter 21 to a next energy application location of the energy application plan. If energy has been applied to all energy application locations defined by the energy application plan, the method ends in step 209.

According to the property determination method described above with reference to FIG. 18, optical information about the tissue surface is used to proceed to the next target spot for ablation, i.e. to proceed to the next energy application location of the energy application plan. Alternatively or in addition, the distal end 22 of catheter 21 can be moved along the line of energy application locations defined by the energy application plan, in order to scan for potential gaps. The control unit can be adapted such that the distal end 22 of the catheter 21 is firstly coarsely guided to the respective energy application location by using, for example, an anatomical map, in particular, an electroanatomical map, an x-ray-image, et cetera of the heart, while the optical sensing data measured by the optical sensor at the distal end 22 of the catheter 21 may be used for the fine-tuning in the positioning of the distal end 22, in particular, of the ablation electrode 4.

Although in an above described embodiment a depth influence value like a lesion depth and a degree of transmurality has been determined based on breaks in horizontal lines in an M-mode image, the property determination unit can also be adapted to determine a depth influence value depending on at least one scatter value being indicative of a scatter of an ultrasound pulse by blood within cardiac tissue, wherein the property determination unit is adapted to determine the at least one scatter value depending on the ultrasound signal.

Figure 19:
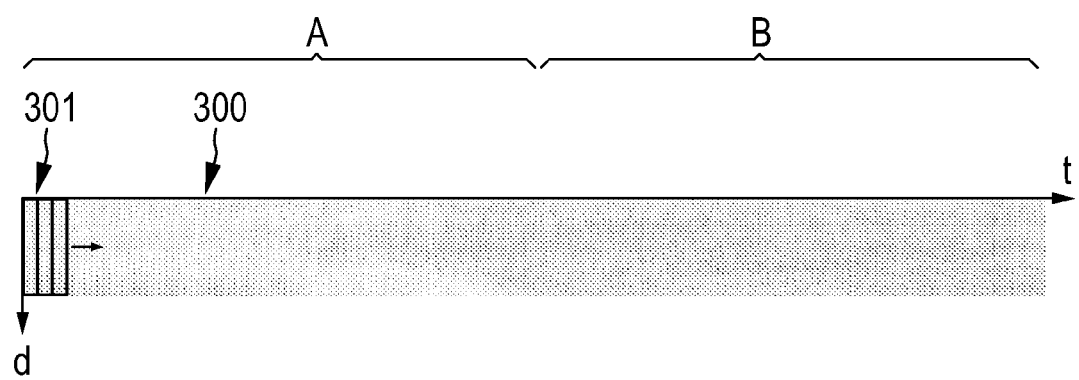
FIG. 19 shows exemplarily an M-mode image of tissue comprising ablated tissue and non-ablated tissue.
Figure 20:
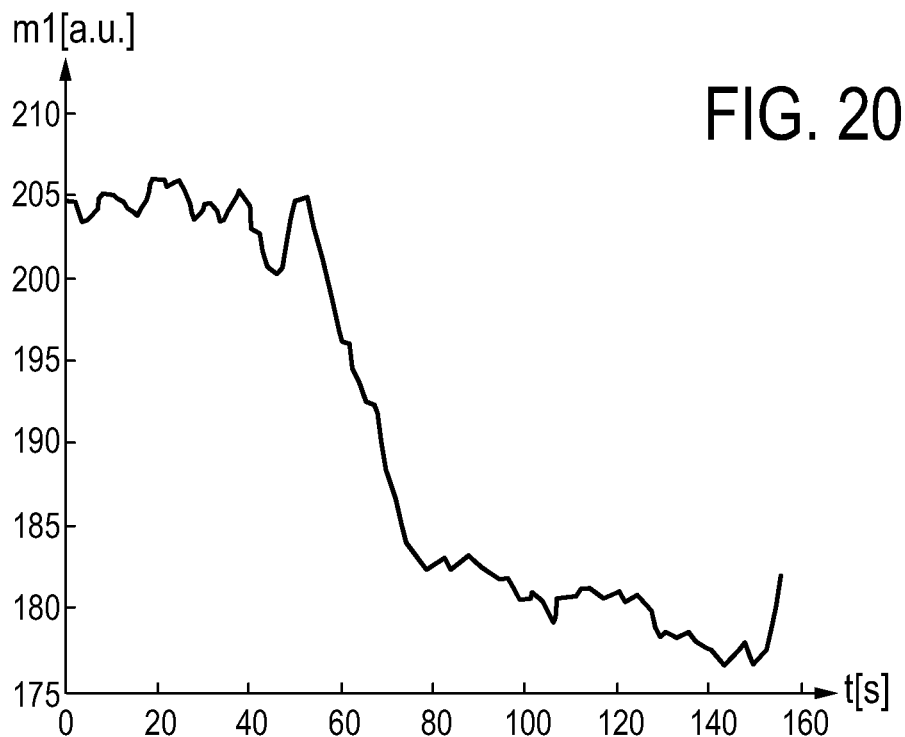
FIGS. 20 to 29 show several scatter values depending on time.
Figure 21:
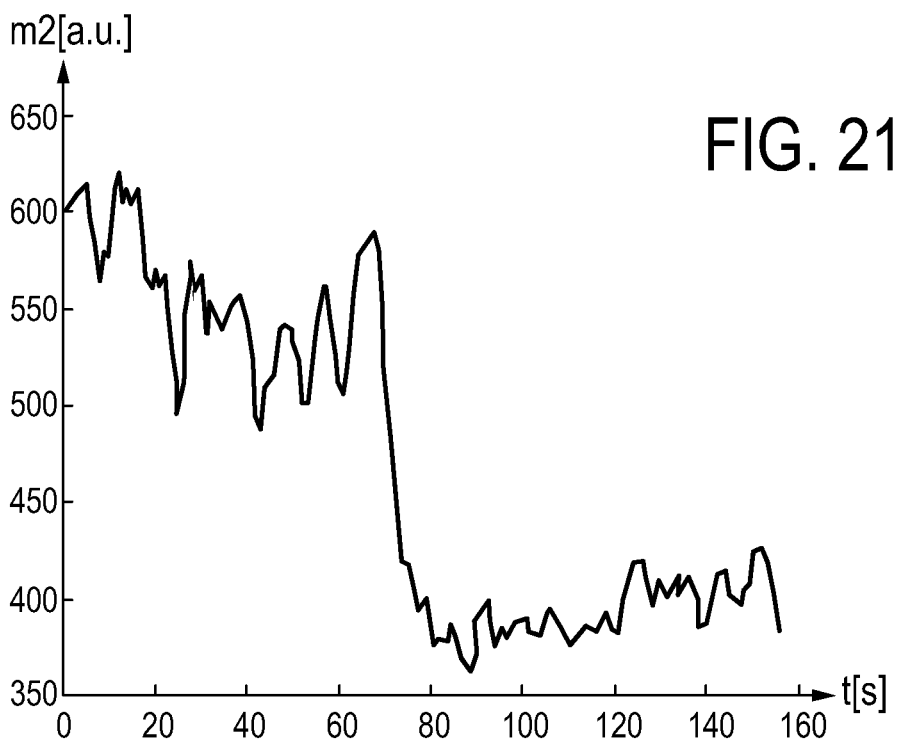
Figure 22:
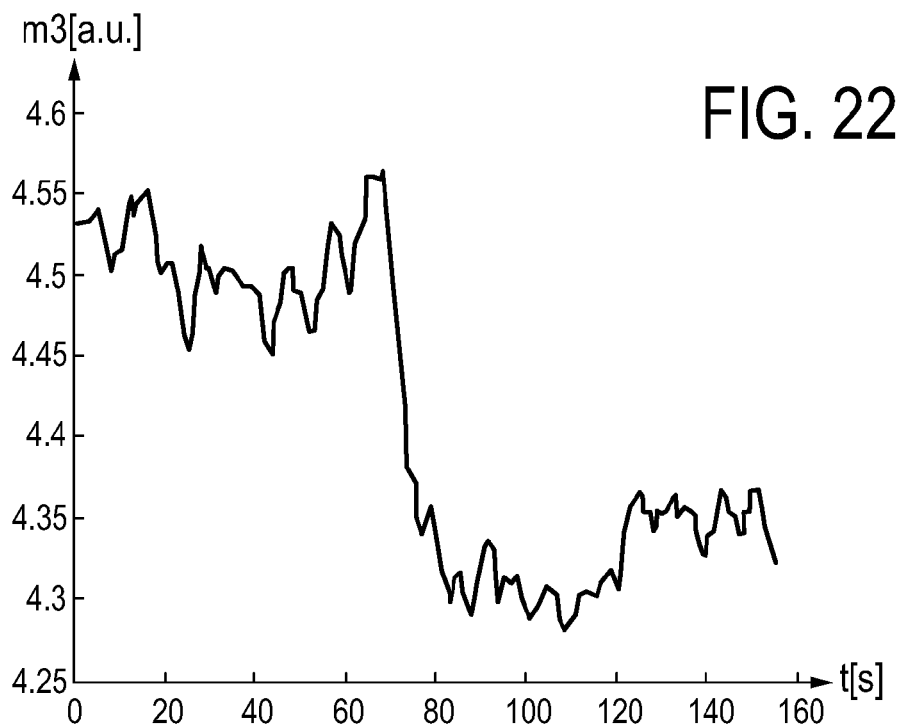
Figure 23:
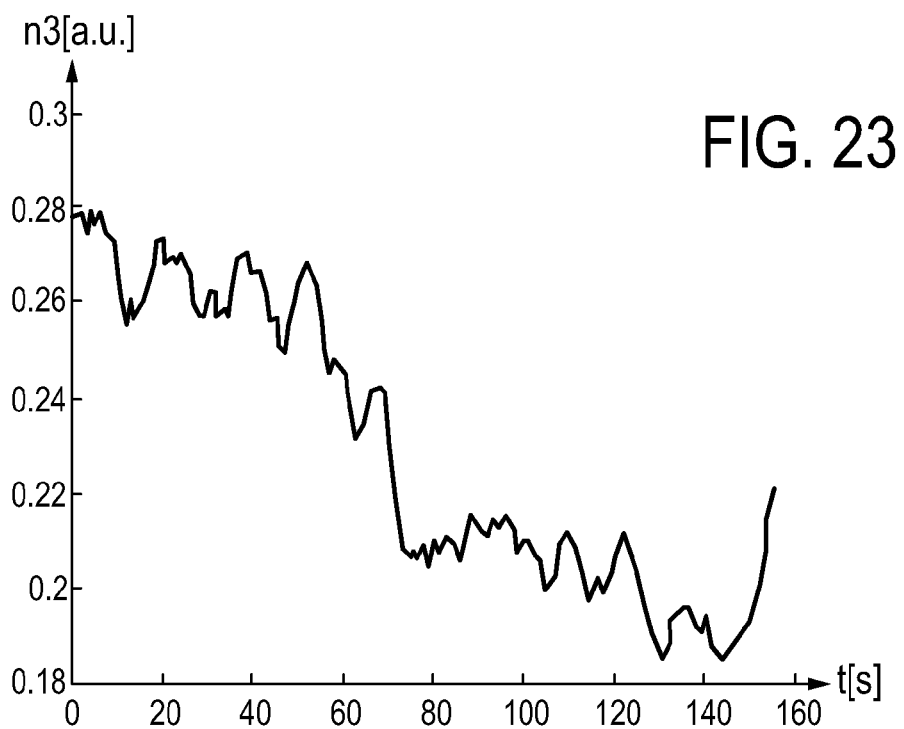
Figure 24:
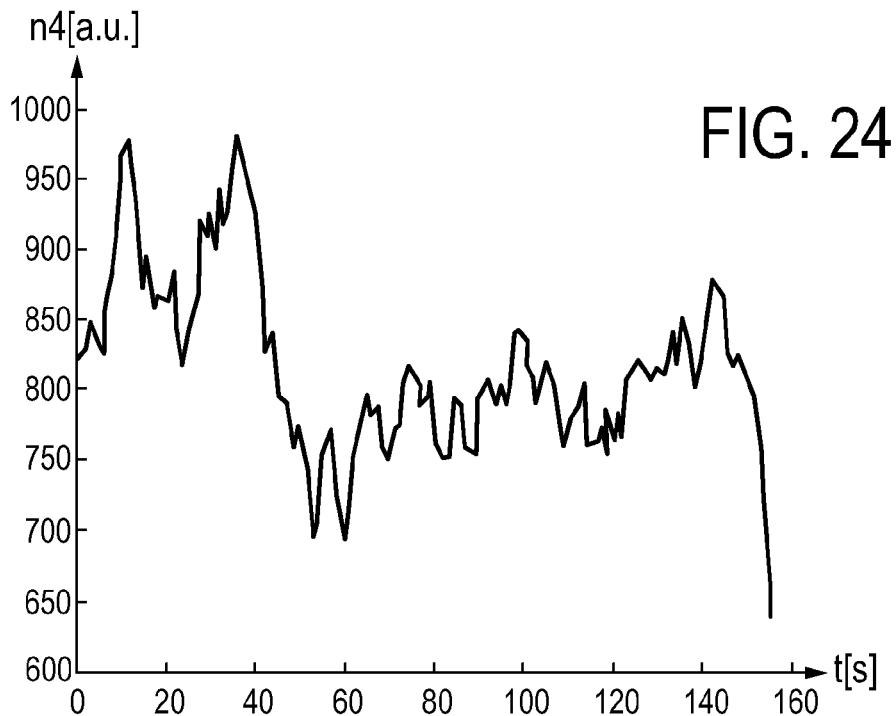
Figure 25:
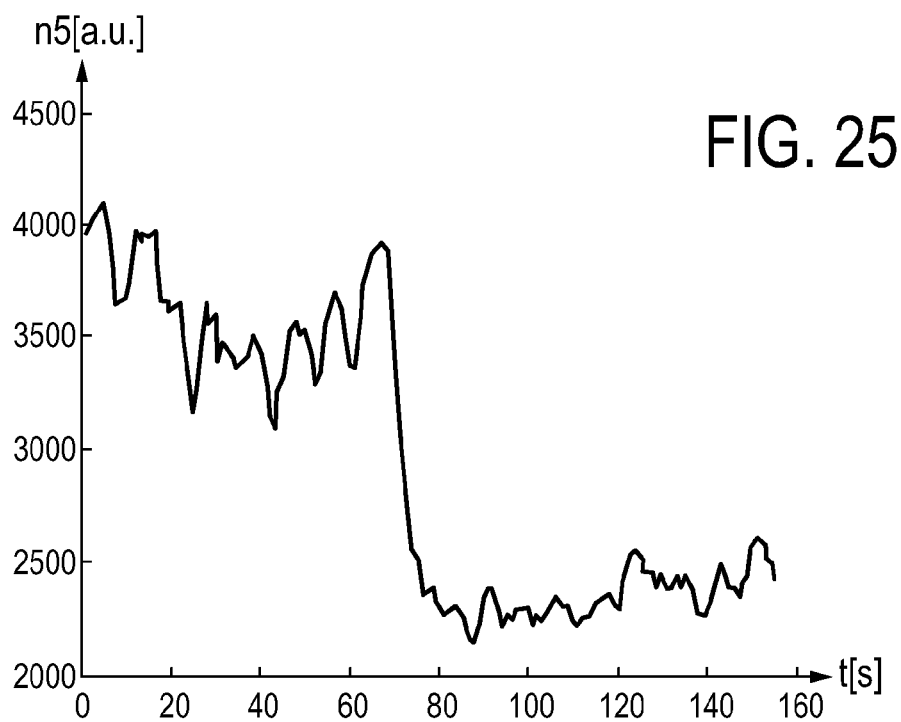
Figure 26:
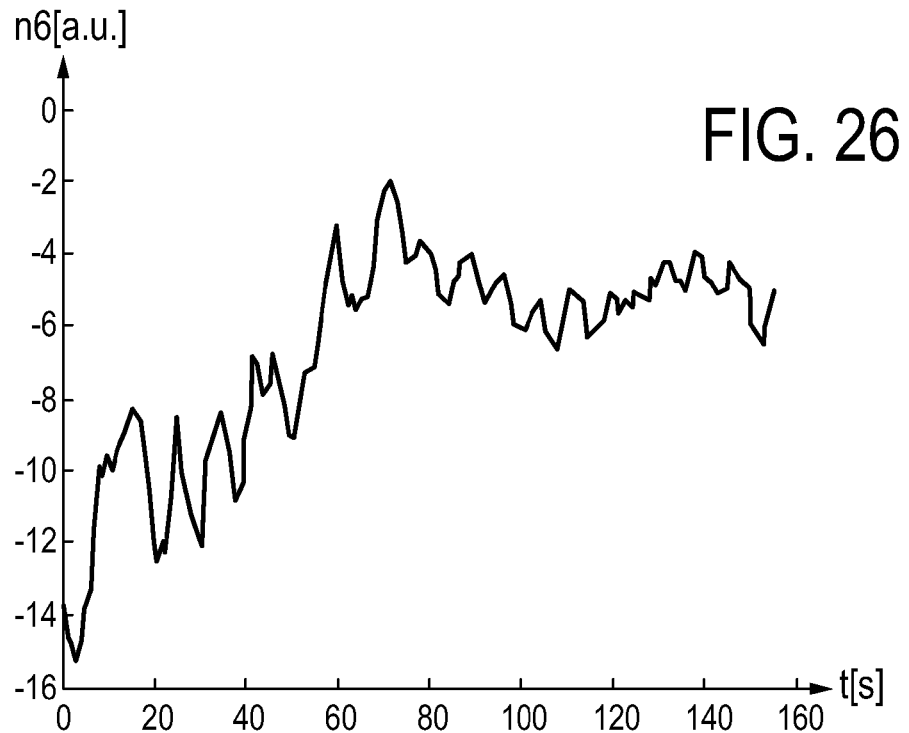
Figure 27:
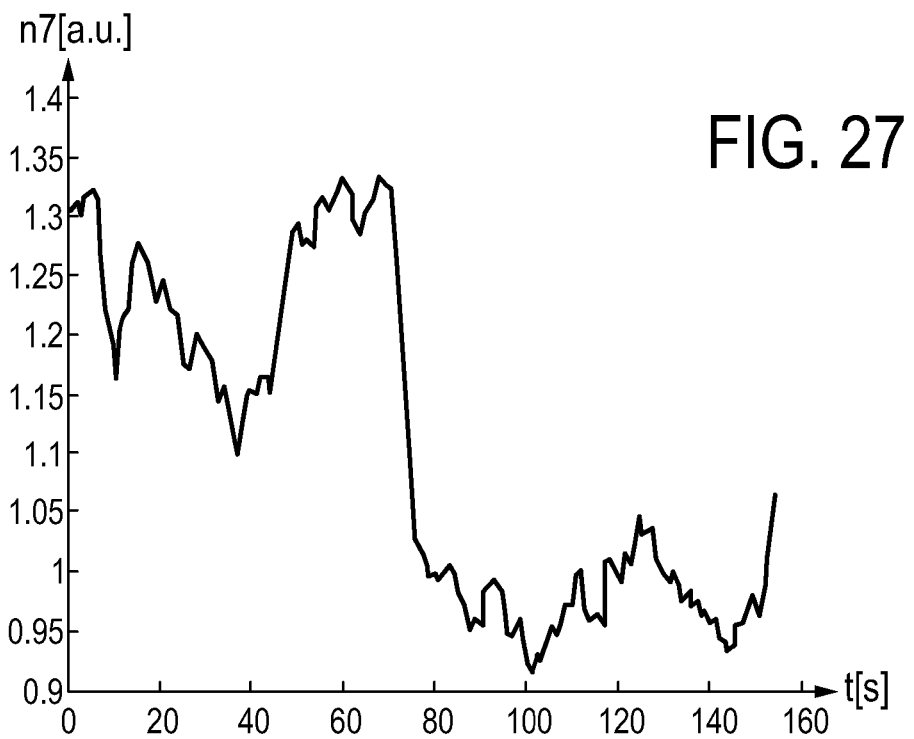
Figure 28:
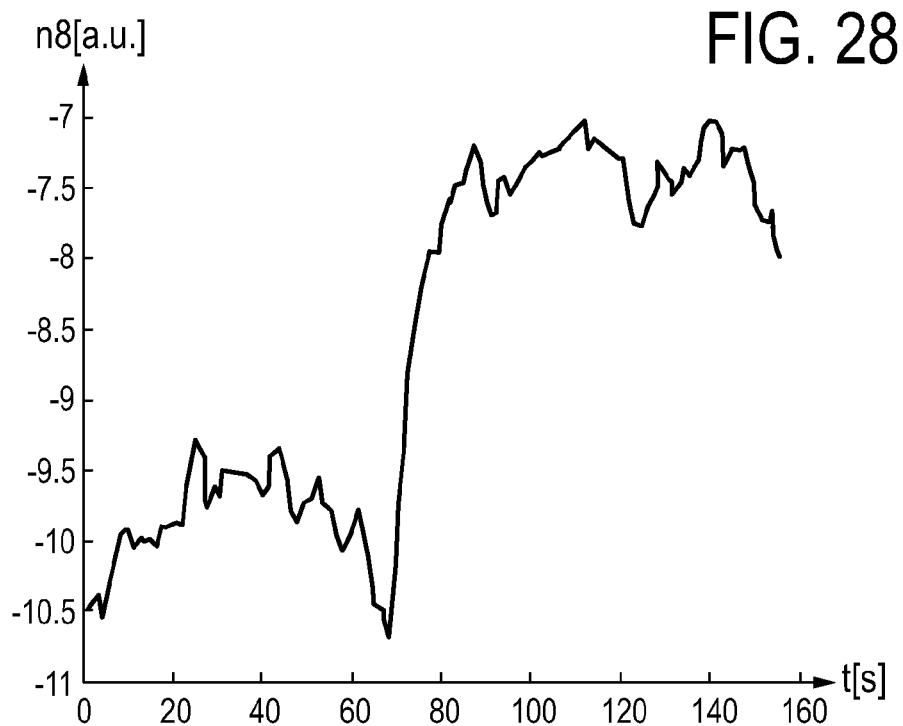
Figure 29:
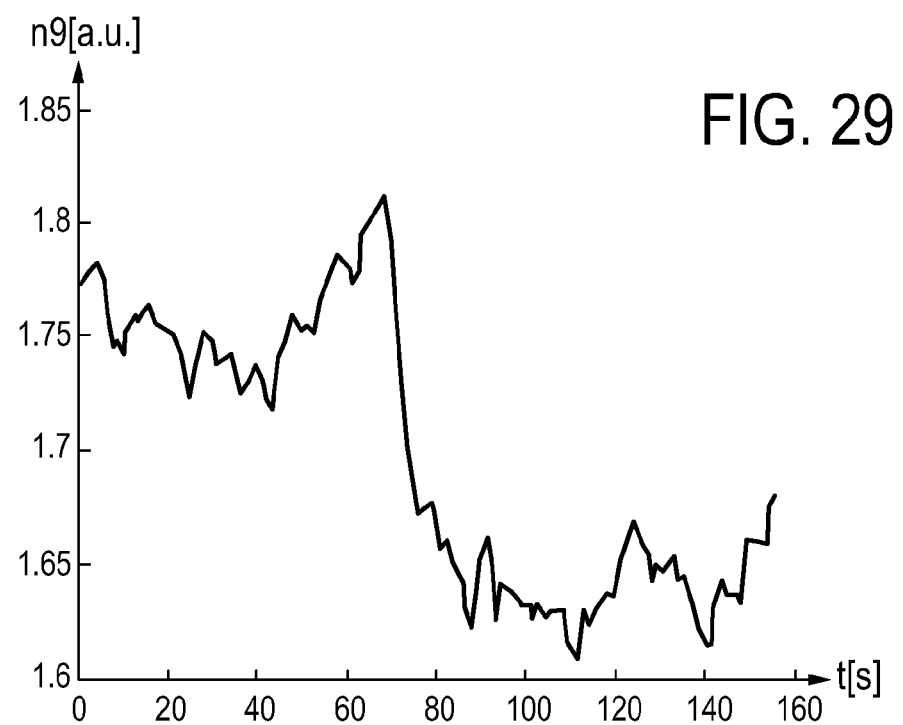

FIG. 19 shows schematically and exemplarily an ultrasound signal 300 being an M-mode image. The M-mode image shows ultrasound intensities of the ultrasound signal depending on different depths d within the tissue depending on the time t. In a first time interval indicated by A the tissue is perfused by blood and in a second time interval indicated by B the tissue is not perfused by blood. The tissue with blood perfusion corresponds to non-ablated tissue and the tissue without blood perfusion corresponds to ablated tissue. The M-mode image is sampled by sample windows 301, which are non-overlapping and which extend along the entire depth range of the M-mode image. The property determination unit is adapted to determine several scatter values for each of the sample windows 301 depending on a histogram of the ultrasound intensities within the respective sample window 301. In particular, the property determination unit is adapted to determine the scatter values based on at least one of a first-order histogram and a second-order histogram. However, also higher-order statistics can be used for determining the scatter values, for example, a Gabor filtering approach can be used for determining the at least one scatter value.

The property determination unit can be adapted to determine several of the following values as scatter values of a respective sample window 301: a first-order mean $m_1$ of a first-order histogram, a first-order variance $m_2$ of the first-order histogram, a first-order entropy $m_3$ of the first-order histogram, a second-order entropy $n_1$ of a second order-histogram, a second-order energy $n_2$ of the second-order histogram, a second-order homogeneity $n_3$ of the second-order histogram, a second-order contrast $n_4$ of the second-order histogram, a second-order cluster tendency $n_5$ of the second-order histogram, a second order-shape $n_6$ of the second-order histogram, a second-order correlation $n_7$ of the second-order histogram and second-order correlation derivatives $n_8$ and $n_9$ of the second-order histogram.

A first-order histogram is a standard histogram, wherein for different ultrasound intensities, i.e. for different ultrasound intensity bins, the number P(I) of pixels having the intensity I, i.e. located in the respective intensity bin, is determined. The first-order mean $m_1$ of this first-order histogram can be defined by following equation:

$$m_1 = \Sigma I P(I), \quad (1)$$

The first-order variance $m_2$ and the first-order entropy $m_3$ can be defined by following equations:

$$m_2 = \Sigma (I - m_1)^2 P(I) \quad (2)$$

and $$m_3 = -\Sigma P(I) \log_2 P(I). \quad (3)$$

In equations (1) to (3) the summation is performed over different ultrasound intensities I.

The second-order values are preferentially based on the so-called co-occurrence matrices, which are, for example, described in the article "Textural Features for Image Classification" by Haralick, Robert M.; Shanmugam, K.; Dinstein, Its'Hak; Systems, Man and Cybernetics, IEEE Transactions on Volume: 3, Issue: 6, Digital Object Identifier: 10.1109/TSMC.1973.4309314, Publication Year: 1973, Page(s): 610-621. The second-order values also consider the relative positions of the ultrasound intensities in the M-mode image and are based on the second-order histogram, which can be defined by following equation:

$$P(i, j) = \frac{\text{number of pixel pairs at a given distance with intensities } i \text{ and } j}{\text{total number of possible pairs}}, \quad (4)$$

wherein the variables i and j indicate ultrasound intensities. The given distance is predefined by, for example, calibration measurements, wherein different predefined distances are tried, until the determined property, which depends on the second-order histogram, matches as good as possible a known property of the object. Preferentially, the given distance is one pixel, i.e. pixel pairs at a given distance are preferentially directly neighbored pixels.

The second-order entropy $n_1$, second-order energy $n_2$, the second-order homogeneity $n_3$, the second-order contrast $n_4$, the second-order cluster tendency $n_5$, the second-order cluster shape $n_6$, the second-order correlation $n_7$ and the second-order correlation derivatives $n_8$, $n_9$ can be defined by following equations:

$$n_1 = -\sum P(i, j) \ln P(i, j). \quad (5)$$

$$n_2 = \sum (i - j)^2 P(i, j), \quad (6)$$

$$n_3 = \sum \frac{P(i, j)^2}{1 + (i - j)^2}, \quad (7)$$

$$n_4 = \sqrt{\sum P^2(i, j)}, \quad (8)$$

$$n_5 = \sum (i + j - 2\mu)^2 P(i, j), \quad (9)$$

where $$\mu = \frac{\Sigma P(i,j)}{N},$$

$$n_6 = \sum (i + j - 2\mu)^3 P(i, j), \quad (10)$$

$$n_7 = \frac{\Sigma (i - \mu)(j - \mu) P(i, j)}{\sigma^2}, \quad (11)$$

where $$\sigma = \frac{1}{N} \sum (i - \mu)^2 \sum P(i, j),$$

$$n_8 = -\sum P(i, j) \ln \left( \sum_i P(i, j) \sum_j P(i, j) \right) \quad (12)$$

and $$n_9 = -\sum \left( \sum_i P(i, j) \sum_j P(i, j) \right) \ln \left( \sum_i P(i, j) \sum_j P(i, j) \right). \quad (13)$$

If not specified otherwise, in equations (5) to (13) the summation is performed over the ultrasound intensities i and j. The logarithms used in equations (5), (12) and (13) can also have another base.

The second-order scatter values provide values being indicative of pattern characteristics of the M-mode image that relates to the spatial arrangement of the pixels of the M-mode image, instead of only the contrast. These second-order statistics describe the randomness, regularities and orientation characteristics of the patterns.

It should be noted that the property determination unit does not necessarily determine all of the above mentioned first-order values and second order-values. Preferentially, the property determination unit is adapted to determine only the kinds of scatter values, which allow determining the desired property of the object. The kinds of scatter values, which can be used for determining the desired property of the object, can be determined by calibration measurements, wherein several kinds of scatter values are determined, while the property of the object is known. In an embodiment, a calibration measurement revealed that the scatter values $m_1$ to $m_3$ and $n_3$ to $n_9$ can be used for determining whether the tissue is ablated or not ablated. These scatter values are schematically and exemplarily shown in FIGS. 20 to 29. In these figures the respective scatter value is shown in arbitrary units depending on the time in seconds. In all of these figures the transition between non-ablated tissue and ablated tissue is visible between about 60 to 80 seconds.

The property determination unit can further be adapted to determine at least one scatter value for a sample window depending on a sum of the ultrasound intensities within the respective sample window and not depending on a histogram. For example, this at least one scatter value can be the sum over all ultrasound intensities within the respective sample window. The at least one scatter value can also be defined by following equation:

$$f = \Sigma I_t I_{t-p}, \quad (14)$$

wherein $I_t$ indicates the ultrasound intensity of a pixel of the M-mode image at the time t and $I_{t-p}$ indicates the ultrasound intensity of a pixel of the M-mode image at the time t−p, wherein p indicates the time between two consecutive heart beats. In equation (14), the summation is performed over all pairs $I_t$ $I_{t-p}$ for which the pixels, which correspond to $I_t$, are located within the respective sample window. The time between two consecutive heartbeats can be determined by an electrocardiograph, which is schematically and exemplarily indicated in FIG. 1 by the box with the reference number 302. In other embodiments, the property determination apparatus may not comprise the electrocardiograph 302 and the time between two consecutive heartbeats may be determined from, for example, the M-mode image.

The property determination unit can be adapted to determine a property of the object depending on the scatter values. In this embodiment, the property determination unit is adapted to determine whether a part of the tissue is ablated tissue or non-ablated tissue based on the scatter values. By ablation the perfusion of the tissue can be modified, wherein the modification of the perfusion modifies the scattering of the ultrasound pulse and, thus, the scatter values. The scatter values can therefore be used for determining whether the tissue is ablated or not ablated.

In this embodiment, the property determination unit is adapted to determine for each of the scatter values of a sample window a voting for the tissue being ablated or the tissue being not ablated. For each of these values the voting is performed by comparing the respective value with a predefined threshold value, i.e. for each of the values a binary thresholding is performed, in order to determine for each value a voting. The property determination unit is adapted to determine the final result, i.e. whether the tissue, which corresponds to the respective sample window, is ablated or not ablated, based on the majority of the votings. This means that, if for a sample window more votings for being ablated than for being non-ablated have been determined, the final result is that the tissue, which corresponds to the respective sample window, is ablated and vice versa. The predefined threshold values can be determined by, for example, calibration measurements.

The property determination unit can also be adapted to combine the several scatter values to a multi-dimensional feature vector, i.e. for each sample window, a multi-dimensional feature vector can be defined, wherein the multi-dimensional feature vector can be compared with a predefined threshold vector for determining whether the respective sample window corresponds to ablated tissue or to non-ablated tissue. Also this predefined threshold vector can be determined by, for example, calibration measurements.

The property determination unit can also be adapted to apply a cluster analysis to the sample windows, wherein the sample windows are clustered depending on the multi-dimensional feature vectors, and to assign properties to the clusters of sample windows. For example, the cluster analysis can result in two clusters of sample windows, wherein the property "ablated tissue" is assigned to one of these clusters and the property "non-ablated tissue" is assigned to the other of the clusters. Whether a cluster represents ablated or non-ablated tissue can be determined depending on a comparison with a threshold, wherein, for example, the multi-dimensional feature vectors of a cluster can be averaged for generating an average vector and wherein the average vector of the cluster can be compared with a threshold vector which can be determined by calibration measurements. Thus, the assignment of properties of the object to the sample windows can be performed by thresholding. It is also possible that the cluster analysis is firstly applied before ablation is started, leading to a first group of clusters representing non-ablated tissue. Then, the cluster analysis can continuously be applied, while the ablation procedure is performed. If the cluster analysis leads to new clusters, which do not belong to the first group of clusters, the property "ablated tissue" can be assigned to these new clusters.

Figure 33:
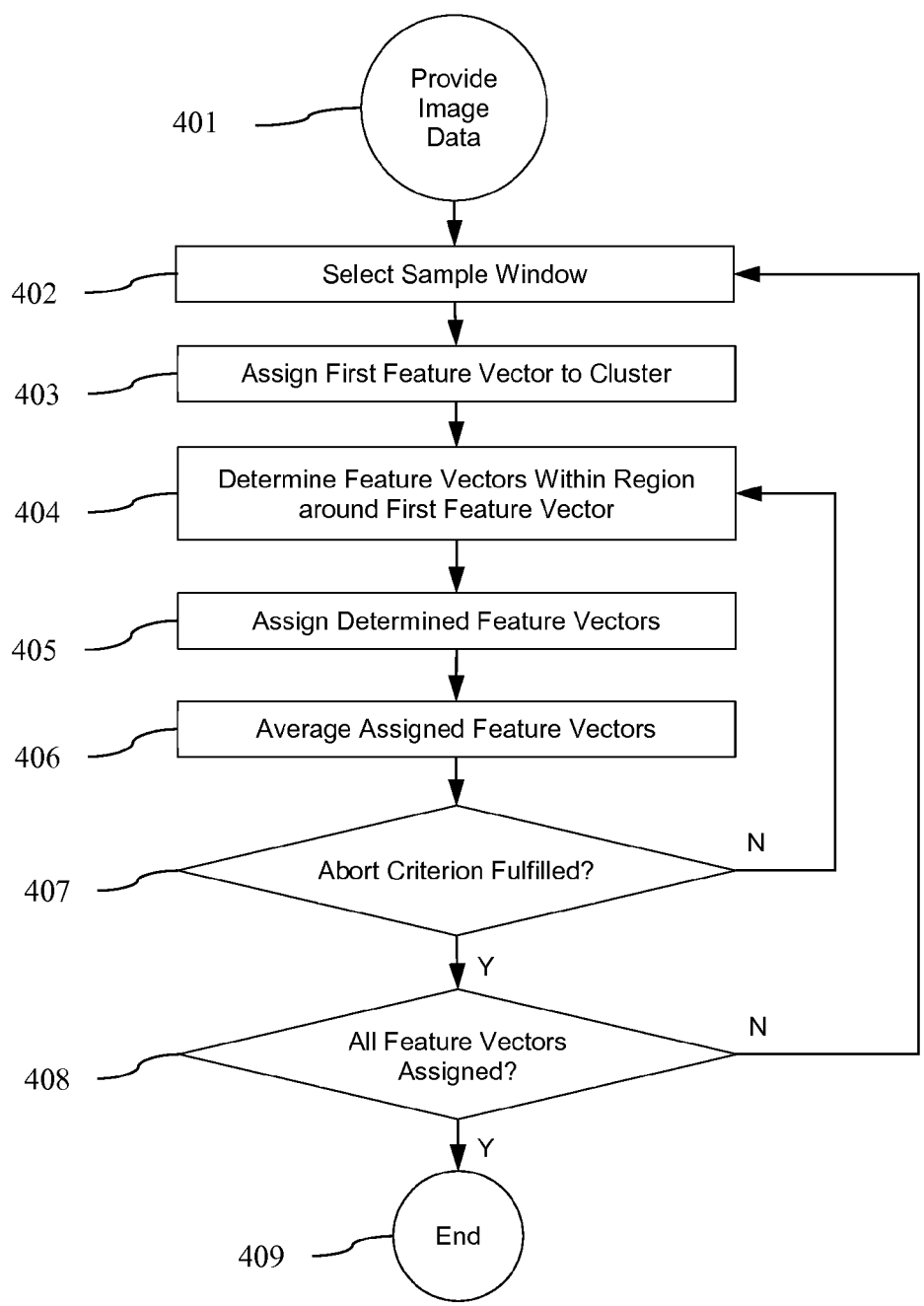
FIGS. 33 and 34 show flowcharts exemplarily illustrating a cluster algorithm.
Figure 34:
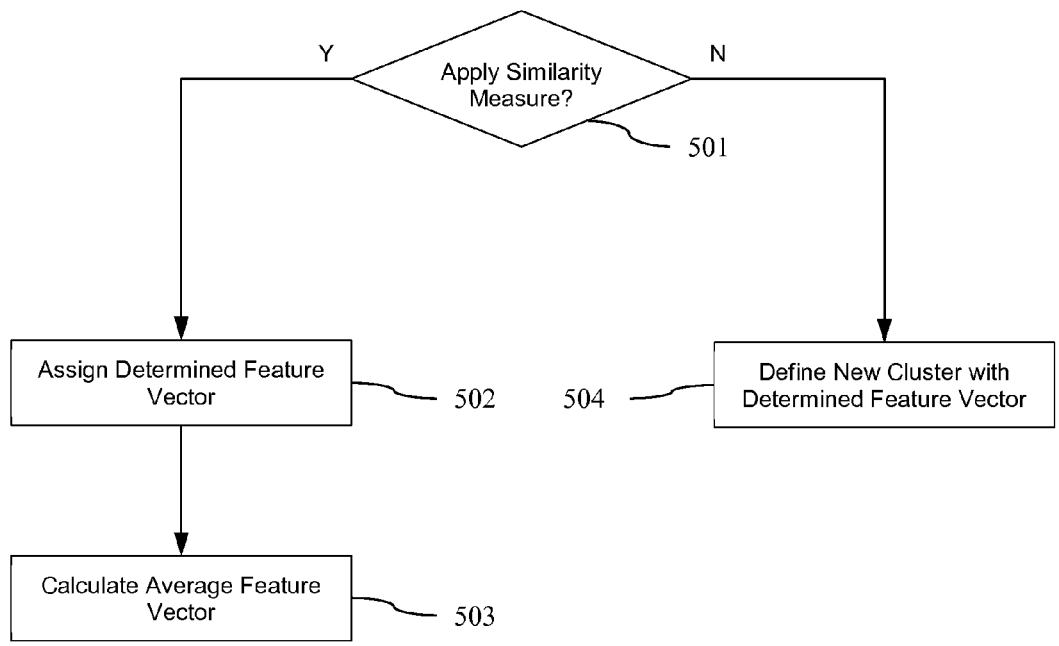

In an embodiment, the property determination unit is adapted to apply following cluster analysis technique for determining which part of the tissue is ablated and which part of the tissue is not ablated. The cluster analysis technique will be described with reference to FIGS. 30 to 34, wherein in FIGS. 30 to 32 the upper part shows an M-mode image and the lower part shows a result of the cluster analysis technique and wherein FIGS. 33 and 34 show flowcharts illustrating several steps of the cluster analysis technique.

The property determination unit determines scatter values for several sample windows 331. The sample windows 331 sample the entire M-mode image and are overlapping. The overlapping of the sample windows 331 increases the resolution of the final clustering result. The sample windows correspond to certain depth ranges and certain time ranges. The sample windows 331 can have the same width and the same length, or the width and the length of the sample windows can be different. Moreover, the M-mode image can be sampled by different sample windows having different sizes and/or different shapes. Preferentially, the width of the window covers at least one heart beat cycle, wherein the sample windows can be aligned with respect to the heart beat. For example, each sample window can start at the same time shift with respect to the respective contraction cycle. In an embodiment, the size of the sample windows in the depth direction is about 0.2 mm.

Figure 30:
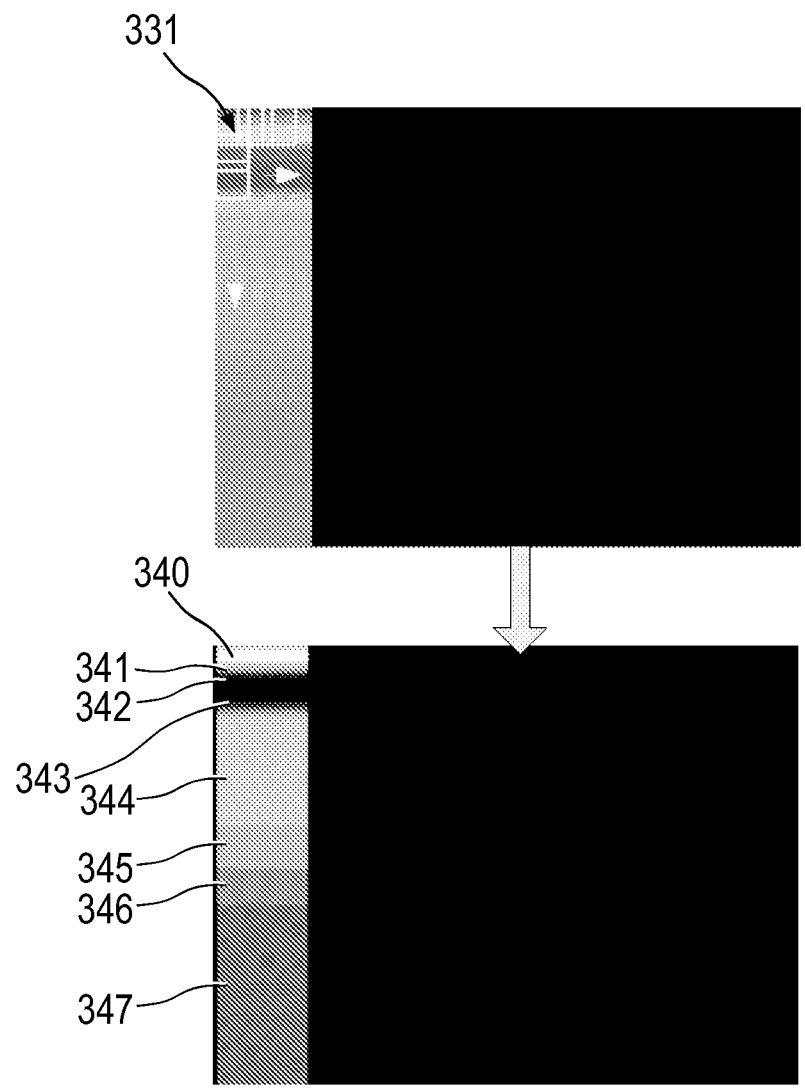
FIGS. 30 to 32 show exemplarily several M-mode images of the object and corresponding cluster results.

A first cluster analysis technique is performed before ablation is started, wherein the corresponding M-mode image is shown in the upper part of FIG. 30. This first cluster analysis technique will be described in the following with reference to the flowchart shown in FIG. 33.

The first cluster analysis technique is initialized in step 401 by providing the M-mode image showing the tissue before ablation is started, by sampling the M-mode image with sample windows and by determining for each of the sample windows a multi-dimensional feature vector comprising scatter values.

In step 402, a sample window and, thus, a corresponding initial feature vector are selected. This selection can be performed randomly. In step 403, the initial feature vector and, thus, the selected sample window are assigned to a first cluster. In step 404, it is determined which feature vectors are arranged within a region around the initial feature vector in the multi-dimensional feature vector space containing the multi-dimensional feature vectors. The region is preferentially a circle, if the feature vector is a two-dimensional vector, or a hypersphere, if the feature vector has a dimension being larger than two. The size of the region can be determined by calibration measurements.

In step 405, the determined feature vectors, which are located within the region around the initial feature vector, are assigned to the first cluster, and, in step 406, the feature vectors within the first cluster are averaged for calculating an average vector of the first cluster. In step 407, it is determined whether an abort criterion is fulfilled. The abort criterion is, for example, whether a predefined number of iterations has already been reached or whether a converging criterion has been met. The converging criterion is, for example, that the difference between the initial feature vector and the average feature vector or the difference between the actually determined average feature vector and a previously determined average feature vector is below a predefined threshold. If the abort criterion is not fulfilled, the cluster analysis performs steps 404 to 407 again, wherein now instead of the initial feature vector the actually determined average feature vector is used, i.e. in step 404 feature vectors are determined within a region around the actually determined average feature vector, in step 405 the feature vectors in the region around the actual average vector, which have not already been assigned to the first cluster, are assigned to the first cluster, and in step 406 a new average feature vector is calculated by averaging the feature vectors of the first cluster.

If in step 407 the abort criterion is fulfilled, the first cluster has been determined and the method continues with step 408. In 408 it is determined whether all feature vectors and, thus, all sample windows have been assigned to a cluster. If not all feature vectors have been assigned to a cluster, steps 402 to 407 are performed based on the remaining feature vectors, which have not been assigned to a cluster, in order to determine a further cluster. Steps 402 to 408 are therefore performed, until all feature vectors and, thus, sample windows have been assigned to a cluster. After all feature vectors have been assigned to a cluster, the first cluster analysis technique ends in step 409. Since the first cluster analysis technique is applied to an M-mode image, which shows the tissue before ablation is started, the clusters, which have been determined by performing steps 401 to 409, correspond to non-ablated tissue.

Figure 31:
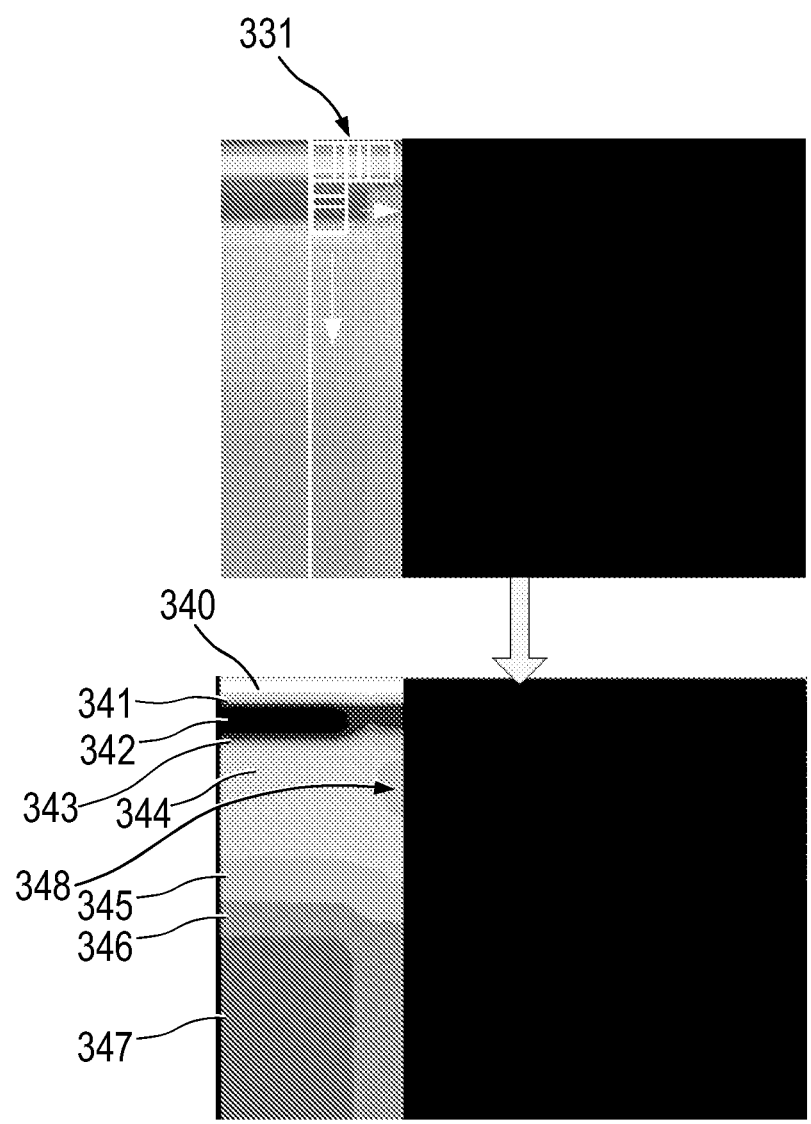
Figure 32:
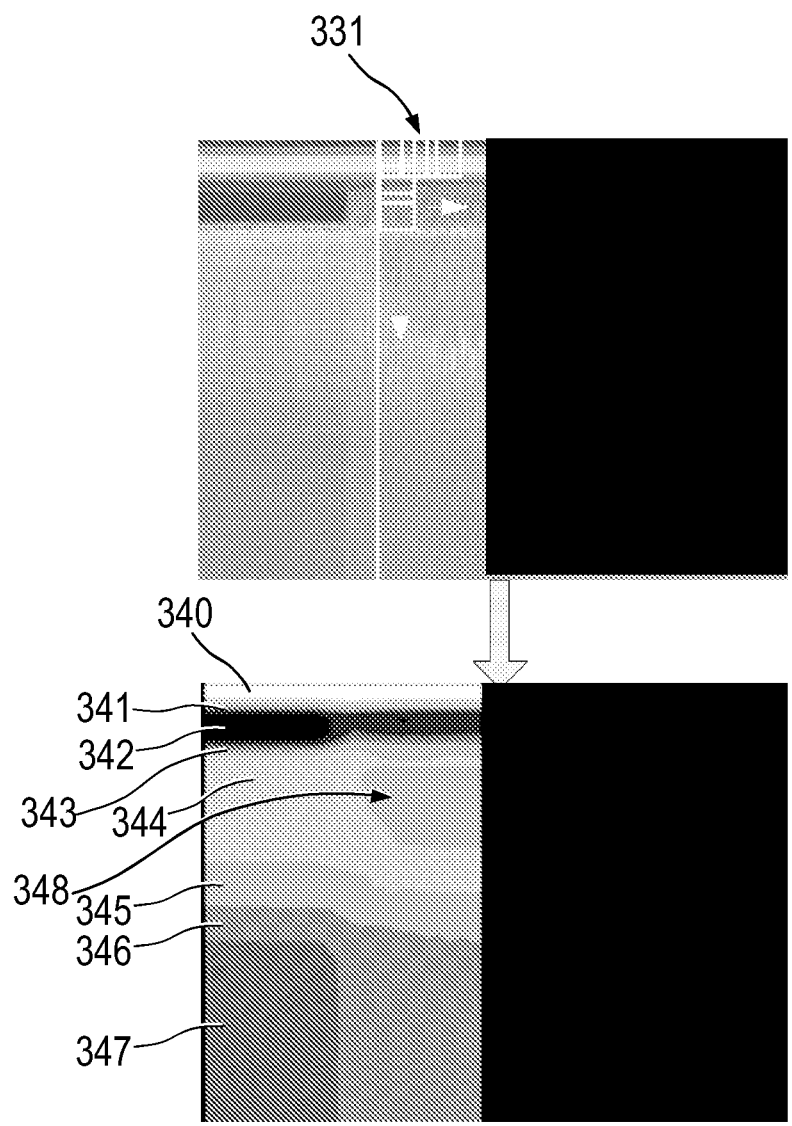

FIGS. 31 and 32 show M-mode images which illustrate the tissue not only before ablation is started, but also after ablation has been started. While the ablation is performed, the ultrasound signal is continuously generated and sampled. Thus, sample windows are continuously acquired and for each sample window a feature vector is calculated, i.e., continuously feature vectors are determined, wherein the continuously newly determined feature vectors are clustered in accordance with a second cluster analysis technique, which will be described in the following with reference to the flowchart shown in FIG. 34.

In step 501, a similarity measure is applied to the actually determined feature vector and to each of the average vectors of the already determined clusters. The similarity measure is, for example, the absolute difference between the actually determined feature vector and the respective average feature vector, wherein, if this absolute difference is below a predefined threshold, the actually determined feature vector is regarded as being similar to the respective average feature vector. If the actually determined feature vector is similar to an average feature vector of a certain cluster, the actually determined feature vector is assigned to the certain cluster in step 502, wherein in step 503 a new average feature vector is calculated for this certain cluster taking into account the newly assigned actually determined feature vector.

If, in step 501, it is determined that the actually determined feature vector is not similar to any of the average feature vectors of the existing clusters, the method continuous with step 504. In step 504, the actually determined feature vector, which could not be assigned to an existing cluster, defines a new cluster and the actually determined feature vector is defined as the average feature vector of this new cluster.

As it can be exemplarily seen in the lower part of FIG. 30, before ablation is started, several clusters 340 . . . 347 are present, which can belong to different structures of non-ablated tissue. In the lower parts of FIGS. 31 and 32 a new cluster 348 can be seen, which is generated, after ablation has been started. The property determination unit assigns this new cluster 348 therefore to "ablated tissue" and the other clusters 340 . . . 347 to "non-ablated".

The property determination unit can further be adapted to determine a lesion depth depending on the determined ablated parts and non-ablated parts. Since from the M-mode image the positions of the ablated parts and the non-ablated parts are known, the lesion depth, i.e. the depth to which the tissue has been ablated starting from an outer surface of the tissue, can easily be determined.

For persons with (paroxysmal) atrial fibrillation the goal of a catheter ablation procedure is preferentially the electrical isolation of the pulmonary veins. In the prior art, catheter ablation procedures are performed with "single-point catheters" such as the Thermocool RF ablation catheter from the company Biosense Webster. Lesion lines can be created with such catheters by sequential point-by-point ablation. In clinical practice, a physician often relies on the representation of ablated sites on an anatomical map, in particular, on an electroanatomical map. Ablated sites are tagged and represented as dots on these maps, and a row of consecutive dots suggests a linear line. However, this method has at least two disadvantages. Firstly, electro-anatomically guided navigation is associated with a considerable spatial error of, for example, 0.5 to 1 cm. This inaccuracy in catheter localization complicates the formation of continuous lesion lines by point-to-point ablation and can result in gaps in lesion lines that appear to be continuous on the electroanatomical map. Secondly, although consecutive ablation dots on a map may suggest that the line is continuous, in reality there are often gaps in the lesion line. The property determination apparatus and the property determination method of the present invention can be adapted to determine whether a lesion line is continuous based on the optical sensing data and whether the tissue is transmural along the lesion line based on the ultrasound sensing data. Thus, the property determination apparatus and the property determination method can be adapted such that both, lesion transmurality and lesion continuity, can be assessed with the same device. From the optical parameters measured at the various fiber endings the orientation of the tip with respect to the tissue surface can be determined. Information on tip orientation can be used as input to determine which of the multiple ultrasound transducers should be assessed for lesion depth monitoring, i.e. which ultrasound transducer is most perpendicular with respect to the tissue surface. This orientation may vary during and between RF delivery. The optical sensors in the ablation electrode, in particular, in the distal end of the catheter, can be used to determine the surface properties of the tissue. Thus, the property determination apparatus and the property determination method can be regarded as a combined device which uses optical imaging to measure tip orientation and surface properties, in particular, lesion continuity, and ultrasound imaging for measuring lesion depth, in particular, transmurality.

Although in the above described embodiments the ultrasound sensing data are used for determining a lesion depth, a degree of transmurality and a contact between the energy application element and the object, the ultrasound sensing data can also be used for determining other properties like slippage or tissue pop.

Although in the above described embodiments certain methods for determining depth influence values, in particular, for determining the lesion depth and the degree of transmurality, have been described, the property determination unit can also be adapted to determine a depth influence value depending on a combination of the above mentioned methods, in particular, to determine the lesion depth and/or the degree of transmurality depending on a combination of, for example, contrast information retrieved from the ultrasound signal, scatter values, spectral data of A-lines, and possible further features which can be retrieved from the ultrasound signal.

The property determination apparatus comprises preferentially an ablation catheter comprising one or more ultrasound transducers which are preferentially individually addressable, wherein the ultrasound transducers are physically confined to the interior of an ablation electrode of the ablation catheter. The ablation electrode allows ultrasound from the ultrasound transducers to pass to the outside of the ablation electrode unperturbed. A plurality of optical fibers with distal ends spatially separated in the tip of the ablation electrode is provided and irrigation fluid can preferentially leave the ablation electrode through irrigation openings in the ablation electrodes, wherein the ultrasound transducers are arranged such within the ablation electrode that they can sense the object through the irrigation openings.

Although in the above described embodiments the catheter comprises a single ablation electrode, i.e. although the above described property determination apparatus can be regarded as being a single-point ablation device, the property determination apparatus can also comprise a catheter having a distal end with several ablation electrodes or other energy application elements for applying ablation energy at different points. Thus, the property determination apparatus can also be a multipoint ablation device like a Pulmonary Vein Ablation Catheter (PVAC).

The property determination apparatus can comprise a catheter used for robotic navigation, for example, used for mechanical or magnetic navigation, like the Lynx catheter from the company Hansen Medical.

Although in the above described embodiments RF is the preferred energy source, also other energy sources can be used like an optical energy source, for example, a laser, a high-intensity focused ultrasound energy source, a microwave energy source or a cryo energy source.

Although in an above described embodiment the distal end of the catheter comprises an electrode for measuring local electrograms, the distal end of the catheter can also comprise other sensing elements like a temperature sensor for applying energy to the object depending on the sensed property of the object, for example, depending on the temperature of the object, or the distal end of the catheter can be adapted to not comprise any element for sensing the object.

The property determination apparatus and the property determination method are preferentially adapted for the treatment of cardiac arrhythmias, the segmentation of scared tissue in the ventricles and/or for ablation treatment in oncology.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Determinations like the determination of a property of the object, for example, the determination of a lesion depth, a degree of transmurality, whether tissue is ablated or non-ablated, whether an energy application element is in contact with the object or not, et cetera. performed by one or several units or devices can be performed by any other number of units or devices. The determinations and/or the control of the property determination apparatus in accordance with the property determination method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a property determination apparatus for determining a property of an object. Optical sensing data being indicative of an optical property of the object and ultrasound sensing data being indicative of an ultrasound property of the object are generated, and a property determination unit determines a property of the object based on at least one of the optical sensing data and the ultrasound sensing data. Since light and ultrasound have generally different penetration depths and scattering properties with respect to the object, a property of the object can be determined with good quality, even if the quality of one of the optical sensing data and the ultrasound sensing data is reduced by, for example, a relatively small penetration depth, or if one of the optical sensing data and the ultrasound sensing data is less suitable for determining a desired property of the object.

The invention claimed is:

1. A property determination apparatus for determining a property of an object, wherein the property determination apparatus (1) comprises:
   an optical sensor (6, 7, 73) for generating optical sensing data being indicative of an optical property of the object (3), wherein the optical sensor comprises optical fibers (6),
   an ultrasound sensor (10) for generating ultrasound sensing data being indicative of an ultrasound property of the object (3),
   an energy application element (4) being an ablation electrode for applying energy to the object (3), wherein the ultrasound sensor (10) and the optical fibers (6) are integrated in the ablation electrode (4),
   a property determination unit (75) for determining a property of the object (3) based on at least one of the optical sensing data and the ultrasound sensing data, wherein the property determination unit (75) is adapted to determine a property of a surface of the object (3) from the optical sensing data,
   wherein the property determination apparatus comprises at least two ultrasound sensors (10) being adapted to sense the object in different sensing directions, wherein the property determination apparatus (1) further comprises an ultrasound sensor selection unit (77) for selecting an ultrasound sensor from the at least two ultrasound sensors (10) depending on the generated optical sensing data and wherein the property determination unit (75) is adapted to determine the property of the object (3) depending on the ultrasound sensing data of the selected ultrasound sensor.

2. The property determination apparatus as defined in claim 1, wherein the property determination apparatus (1) comprises a catheter (21), wherein the optical sensor (6) and the ultrasound sensor are integrated in the catheter (21).

3. The property determination apparatus as defined in claim 1, wherein the property determination unit (75) is adapted to determine a depth influence value being indicative of a depth to which the object (3) has been influenced by the applied energy from the ultrasound sensing data.

4. The property determination apparatus as defined in claim 1, wherein the ultrasound sensor selection unit (77) is adapted to determine the orientations of the sensing directions relative to the object (3) from the optical sensing data and to select an ultrasound sensor based on the determined orientations.

5. The property determination apparatus as defined in claim 4, wherein the ultrasound sensor selection unit (77) is adapted to select the ultrasound sensor of which the sensing direction is most perpendicular to a surface of the object (3).

6. The property determination apparatus as defined in claim 1, wherein the property determination apparatus (1) further comprises a display (10) for displaying at least one of the optical sensing data, the ultrasound sensing data, and the determined property of the object (3).

7. The property determination apparatus as defined in claim 6, wherein energy is applied to the object (3) at an energy application location on the object (3), wherein the optical sensor is adapted to generate optical sensing data being indicative of an optical property of the object (3) at the energy application location, wherein the ultrasound sensor is adapted to generate ultrasound sensing data at the energy application location, wherein the property determination unit (75) is adapted to determine a property of the object (3) based on at least one of the optical sensing data and the ultrasound sensing data at the energy application location, wherein the property determination apparatus further comprises:
   a storage unit (78) for storing at least one of the optical sensing data, the ultrasound sensing data and the determined property,
   an image providing unit (2) for providing an image of the object, wherein the display is adapted to display the energy application location on the image,
   a user interface (79) for allowing a user to select the shown energy application location, wherein the display is adapted to display at least one of the optical sensing data, the ultrasound sensing data and the determined property, if the displayed energy application location has been selected by the user.

8. The property determination apparatus as defined in claim 1, wherein
   the property determination apparatus (1) further comprises:
   an energy application plan providing unit (84) for providing an energy application plan comprising energy application locations at which energy is to be applied to the object (3),
   a contact determination unit (15) for determining whether the energy application element (4) is in contact with the object (3) based on the ultrasound sensing data,
   a moving unit (29) for moving the energy application element (4), the optical sensor and the ultrasound sensor to an energy application location of the energy application plan,
   a control unit (85) for controlling the property determination apparatus in accordance with following steps:
   a) providing an energy application plan comprising energy application locations at which energy is to be applied to the object (3) by the energy application plan providing unit (201),
   b) moving the energy application element (4), the optical sensor and the ultrasound sensor to an energy application location of the energy application plan by the moving unit (202),
   c) generating ultrasound sensing data at the energy application location by the ultrasound sensor,
   d) determining whether the energy application element (4) is in contact with the object (3) at the energy application location based on the ultrasound sensing data, wherein, if the energy application element (4) is not in contact with the object, the position of the energy application element is modified by the moving unit (202) and steps c) and d) are repeated, until the energy application element (4) is in contact with the object (3),
   e) generating optical sensing data at the energy application location by the optical sensor,
   f) determining whether the object (3) has already been influenced by energy at the energy application location by the property determination unit (75) depending on the optical sensing data, wherein, if the object (3) has already been influenced by energy at the energy application location, the method continuous with step b) for moving the energy application element (4), the optical sensor and the ultrasound sensor to a next energy application location of the energy application plan, g) applying energy to the object (3) at the energy application location, h) generating ultrasound sensing data at the energy application location by the ultrasound sensor, i) determining whether the object (3) has been influenced by energy to a predefined degree at the energy application location by the property determination unit (75) depending on the ultrasound sensing data, wherein steps g) to i) are repeated, until the object (3) has been influenced by energy to the predefined degree at the energy application location, j) repeating steps b) to i) with a next energy application location of the energy application plan until energy has been applied to all energy application locations of the energy application plan.

9. A property determination method for determining a property of an object, wherein the property determination method comprises:

generating optical sensing data being indicative of an optical property of the object by an optical sensor, wherein the optical sensor comprises optical fibers, generating ultrasound sensing data being indicative of an ultrasound property of the object by an ultrasound sensor, applying energy to the object by an energy application element being an ablation electrode, wherein the ultrasound sensor and the optical fibers are integrated in the ablation electrode, determining a property of the object based on at least one of the optical sensing data and the ultrasound sensing data by a property determination unit, wherein the property determination unit determines a property of a surface of the object from the optical sensing data, wherein the property determination apparatus comprises at least two ultrasound sensors (10) being adapted to sense the object in different sensing directions, wherein the method further comprising the step of an ultrasound sensor selection unit (77) selecting an ultrasound sensor from the at least two ultrasound sensors (10) depending on the generated optical sensing data, and wherein the property determination unit (75) is adapted to determine the property of the object (3) depending on the ultrasound sensing data of the selected ultrasound sensor.

10. A computer program product for determining a property of an object, the computer program product comprising a non-transient computer readable storage medium having encoded thereon program steps for acquiring optical sensing data being indicative of an optical property of the object from an optical sensor, wherein the optical sensor comprises optical fibers, acquiring ultrasound sensing data being indicative of an ultrasound property of the object from an ultrasound sensor, applying energy to the object by an energy application element being an ablation electrode, wherein the ultrasound sensor and the optical fibers are integrated in the ablation electrode, determining a property of the object based on at least one of the optical sensing data and the ultrasound sensing data by a property determination unit, wherein the property determination unit determines a property of a surface of the object from the optical sensing data, wherein the property determination apparatus comprises at least two ultrasound sensors (10) being adapted to sense the object in different sensing directions, wherein the method further comprising the step of an ultrasound sensor selection unit (77) selecting an ultrasound sensor from the at least two ultrasound sensors (10) depending on the generated optical sensing data, and wherein the property determination unit (75) is adapted to determine the property of the object (3) depending on the ultrasound sensing data of the selected ultrasound sensor.

\* \* \* \* \*